(12) United States Patent
Evans

(10) Patent No.: US 12,315,639 B2
(45) Date of Patent: May 27, 2025

(54) METHODS AND APPARATUS FOR REDUCING THE RISK, AND IDENTIFYING THE EXISTENCE, OF NEUROLOGICAL INJURY TO A HUMAN FETUS DURING AND BEFORE LABOR

(71) Applicant: Mark Evans, Las Vegas, NV (US)

(72) Inventor: Mark Evans, Las Vegas, NV (US)

(*) Notice: Subject to any disclaimer, the term of this patent is extended or adjusted under 35 U.S.C. 154(b) by 364 days.

(21) Appl. No.: 17/632,011

(22) PCT Filed: Aug. 3, 2020

(86) PCT No.: PCT/US2020/044768
§ 371 (c)(1),
(2) Date: Feb. 1, 2022

(87) PCT Pub. No.: WO2021/022254
PCT Pub. Date: Feb. 4, 2021

(65) Prior Publication Data
US 2022/0277853 A1    Sep. 1, 2022

Related U.S. Application Data

(60) Provisional application No. 62/881,701, filed on Aug. 1, 2019.

(51) Int. Cl.
*G16H 50/30*    (2018.01)
*A61B 5/00*    (2006.01)

(52) U.S. Cl.
CPC ............ *G16H 50/30* (2018.01); *A61B 5/4356* (2013.01)

(58) Field of Classification Search
None
See application file for complete search history.

(56) References Cited

U.S. PATENT DOCUMENTS 3,989,034 A    11/1976    Hojaiban
4,821,732 A     4/1989    Lippes
(Continued)

FOREIGN PATENT DOCUMENTS

CA    2604420    10/2009
CN    105917232    8/2016
(Continued)

OTHER PUBLICATIONS

European Patent Office; Extended Search Report Communication pursuant to Rule 62 EPC; Jun. 7, 2020, Application No. 17872197.3-1115/3541276 PCT/2017062820, Ref. DD/P27504EP.
(Continued)

*Primary Examiner* — Ankit D Tejani
(74) *Attorney, Agent, or Firm* — Dickinson Wright PLLC

(57) ABSTRACT

Methods and apparatus for reducing the risk of neurological injury to a human fetus during labor and before are disclosed, which include the steps of: (1) identifying during labor the risk of neurological injury to a fetus by, conducting an analysis of fetal blood to determine at least a first base excess (BE) value for the fetus; (2) determining a multiple of the median for the BE value at the first period in time, wherein a risk of neurological injury to the fetus is indicated when the BE value is a predefined multiple of a median BE value; and (3) treating the fetus for which the risk of neurological injury is, by intervening in labor to reduce or eliminate the risk of neurological injury to the fetus through any conventional therapeutic measures.

20 Claims, 21 Drawing Sheets

(56) References Cited

U.S. PATENT DOCUMENTS

| | | |
|---|---|---|
| 4,951,680 A | 8/1990 | Kirk |
| 5,069,218 A | 12/1991 | Ikeda |
| 5,088,497 A | 2/1992 | Ikeda |
| 5,123,420 A | 6/1992 | Paret |
| 5,425,362 A | 6/1995 | Siker |
| 5,433,204 A | 7/1995 | Olson |
| 5,442,940 A | 8/1995 | Secker |
| 5,466,215 A | 11/1995 | Lair |
| 5,474,065 A | 12/1995 | Meathrel |
| 5,497,317 A | 3/1996 | Hawkins |
| 5,511,553 A | 4/1996 | Segalowitz |
| 5,596,993 A | 1/1997 | Oriol |
| 5,623,939 A | 4/1997 | Garfield |
| 5,851,188 A | 12/1998 | Bullard |
| 5,954,663 A | 9/1999 | Gat |
| 5,957,855 A | 9/1999 | Oriol |
| 6,024,701 A | 2/2000 | Almog |
| 6,254,537 B1 | 7/2001 | Nguyen |
| 6,340,346 B1 | 1/2002 | Almog |
| 6,423,016 B1 | 7/2002 | Hamilton |
| 6,434,418 B1 | 8/2002 | Neal |
| 6,522,916 B1 | 2/2003 | Kwon |
| 6,751,498 B1 | 6/2004 | Greenberg |
| 7,113,819 B2 | 9/2006 | Hamilton |
| 7,313,424 B2 | 12/2007 | Mayevsky |
| 7,314,451 B2 | 1/2008 | Halperin |
| 7,333,850 B2 | 2/2008 | Marossero |
| 7,850,625 B2 | 12/2010 | Paltieli |
| 9,078,582 B2 | 7/2015 | Tupin, Jr. |
| 9,131,860 B2 | 9/2015 | Evans |
| 2003/0187364 A1 | 10/2003 | Hamilton |
| 2005/0267377 A1 | 12/2005 | Marossero |
| 2006/0074329 A1 | 4/2006 | Ferguson |
| 2007/0213627 A1 | 9/2007 | James |
| 2007/0255588 A1 | 11/2007 | Hamilton |
| 2010/0168528 A1 | 7/2010 | Evans |
| 2010/0268124 A1 | 10/2010 | Hamilton |
| 2011/0071414 A1 | 3/2011 | Heil |
| 2013/0281861 A1 | 10/2013 | Flomerfelt |
| 2015/0094263 A1 | 4/2015 | Caggiano et al. |
| 2015/0157276 A1 | 6/2015 | Gratacos et al. |
| 2016/0354043 A1 | 12/2016 | Heil |
| 2017/0003304 A1 | 1/2017 | Demirdjian et al. |
| 2017/0308662 A1 | 10/2017 | Hamilton |

FOREIGN PATENT DOCUMENTS

| | | |
|---|---|---|
| CN | 107480419 | 12/2017 |
| EP | 0384339 | 8/1990 |
| EP | 1568316 | 8/2005 |
| JP | 2015-519107 A | 7/2015 |
| JP | 2017-507317 A | 3/2017 |
| WO | WO 9849942 | 11/1998 |
| WO | WO 0001117 | 1/2000 |
| WO | WO2005096707 | 10/2005 |
| WO | WO 07120873 | 10/2007 |
| WO | WO2012/101268 A | 8/2012 |
| WO | 2018094398 | 5/2018 |

OTHER PUBLICATIONS

Intermittent Auscultation for Intrapartum Fetal Heart Rate Surveillance; Journal of Midwifery & Women's Health; Mar. 2010; No. 11; pp. 397-403; Elsevier Inc; Silver Spring, MD.

International Search Report, for International Application No. PCT/US2017/62820; Jan. 17, 2018.

Written Opinion of the International Searching Authority for International Application No. PCT/US2017/62820; Jan. 17, 2018.

Murray, Deidre M.; Fetal Heart Rate Patterns in Neonatal Hypoxic-Iscemic Encephalopathy: Relationship with Early Cerebral Activity and Neurodevelopmental Outcome; American Journal of Perinatology; vol. 26, No. 8; 2009.

Yuki Kodama, et al.; Intrapartum fetal heart rate patterns in infants with (>34 weeks) with poor neurological outcome; Early Human Development 85 (2009, pp. 235-238.

Parer, et al.; A framework for standardized management of intrapartum fetal heart rate patterns, American Journal Obst & Gyn; Jul. 2007, pp. 26.e1-6.

Parer, JT; FHR Monitoring; Can we expect improvements soon ?; Maternal Fetal Medicine, University of California San Francisco, MFM Fellows Video conference Series, May 21, 2008.

Leung et al.; Head-to-body delivery interval and risk of fetal acidosis and hypoxic ischaemic encephalopathy in shoulder dystocia; a retrospective review, BJOG An Internal Journal of Obs & Gyn, 2011. Retrieved on Nov. 14, 2020. Retrieved from <URL: https://obgyn.onlinelibrary.wiley.com/doi/pdf/10.111/j.1471-0528.2010.02834.x>entire document.

Nanda et al.; Maternal serum adiponectin at 11 to 13 weeks of gestation in the prediction of macrosomia, prenantel diagnosis, vol. 31, Issue 5, May 2011. Retrieved on Nov. 14, 2020. Retrieved from <https://obgyn.onlinelibrary.wiley.com/doi/abs/10.1002/pd.2723>entire document.

Uccella S et al.; Prediction of fetal base excess values at birth using an algorithm to interpret fetal heart rate tracings: a retrospective validation. BJOG. Dec. 2012;119(13):1657-64. doi: 10.1111/j.1471-0528.2012.03511.x. Epub Oct. 12, 2012. PMID: 23061674.

Eden Robert D, Evans Mark I, et al; The "Fetal Reserve Index": Re-Engineering the Interpretation and Responses to Fetal Heart Rate Patterns; 2018;43(2):90-104. doi: 10.1159/000475927. Epub Jun. 8, 2017. PMID: 28591756; Fetal Diagn Ther.

Leung Ty, Head-to-body delivery interval and risk of fetal acidosis and hypoxic ischaemic encephalopathy in shoulder dystocia: a retrospective review. BJOG. Mar. 2011;118(4):474-9. doi: 10.1111/j.1471-0528.2010.02834.x. Epub Dec. 24, 2010. PMID: 21199293.

FIG. 7

| FRI | FRI change | N | PIOI PIOh | PhOI PhOh | FRI B (sig)* | FRI chg B (sig) | # (%) of cases no chg or positive / % drop between starting dilatation and CD=10 | N's R² (sig) HL0 | Sens | Spec | PLR | NLR | PPV | NPV |
|---|---|---|---|---|---|---|---|---|---|---|---|---|---|---|
| FRI4f | FRI10f-4f chg | 30 | 2 / 5 | 0 / 23 | -12.56 (.020) | -8.13 (.071) | 1 (6.7%) / 50% | .32 (.029) HL(.277) | 29 | 100 | | .71 | 100 | 82 |
| FRI5f | FRI10f-5f chg | 62 | 12 / 9 | 6 / 35 | -6.35 (.015) | -8.10 (.001) | 8 (13%) / 41% | .32 (.000) HL(.947) | 57 | 85 | 3.90 | .50 | 67 | 80 |
| FRI6f | FRI10f-6f chg | 56 | 12 / 8 | 30 | -10.08 (.003) | -7.04 (.001) | 5 (9%) / 27% | .39 (.000) HL(.913) | 60 | 83 | 3.60 | .48 | 67 | 79 |
| FRI7f | FRI10f-7f chg | 34 | 5 / 6 | 3 / 20 | -11.21 (.002) | -8.44 (.002) | 3 (9%) / 27% | .44 (.002) HL(.276) | 46 | 87 | 3.48 | .63 | 63 | 77 |

| FRI | FRI change | N | True + False - Classification | False + True - Table | FRI B (sig)* | FRI chg B (sig) | # (%) of cases no chg or positive Mean (sd), Md | N's R² (sig) HL0 | Sens | Spec | PLR | NLR | PPV | NPV |
|---|---|---|---|---|---|---|---|---|---|---|---|---|---|---|
| FRI4f | FRI10f-4f chg | 30 | 2 / 5 | 0 / 23 | -12.56 (.020) | -8.13 (.071) | 1 (6.7%) -.35(.16), -.38 | .32 (.029) HL(.277) | | | | | | |
| FRI5f | FRI10f-5f chg | 62 | 13 / 10 | 6 / 33 | -35.30 (.015) | -8.10 (.001) | 8 (13%) -.32(.20), -.38 | .38(.000) HL(.618) | 57 | 85 | 3.67 | .51 | 77 | 75 |
| FRI6f | FRI10f-6f chg | 56 | 10 / 10 | 8 / 28 | -10.08 (.003) | -7.04 (.001) | 5 (9%) -.35(.18), -.38 | .20(.013) HL(.893) | 50 | 78 | 2.25 | .64 | 74 | 68 |
| FRI7f | FRI10f-7f chg | 34 | 3 / 7 | 1 / 23 | -4.31 (.018) | -5.91 (.018) | 3 (9%) -.29(.18), -.25 | .19 (.09) HL(.487) | 30 | 96 | 7.20 | .73 | 77 | 77 |

FIG. 8

METHODS AND APPARATUS FOR REDUCING THE RISK, AND IDENTIFYING THE EXISTENCE, OF NEUROLOGICAL INJURY TO A HUMAN FETUS DURING AND BEFORE LABOR

CROSS-REFERENCE TO RELATED APPLICATIONS

The present application is related to, and claims the benefit of priority from, U.S. Provisional Application Ser. No. 62/881,701, filed 1 Aug. 2019, the disclosure of which is incorporated herein by reference in its entirety.

FIELD OF THE INVENTION

The present invention pertains to the field of obstetrics and, more specifically, to methods and apparatus for reducing the risk of neurological injury to a human fetus during and before labor.

BACKGROUND

Current methods for assessing fetal health and predicting risk of neurologic compromise using the American College of Obstetricians and Gynecologist's (ACOG) "Category System" are very poor, missing as much as 50% of cerebral palsy (CP) cases. Its use has led to significant increases in the Cesarean Delivery Rate (CDR), with little to no impact on reducing severe complications such as CP. The statistical performance metrics of the Category System violate essentially all of the key standard principles required for an effective screening program. ACOG's Category III, which is the point of required action to deliver, or at least treat, the fetus is so far to the right on the distribution curve of values that it has a high positive predictive value for damage—much of which may have already occurred. It also has a very high and unacceptable false negative rate—with 50% of serious cases missed (as reported in multiple publications). Conversely, ACOG's Category II, which is defined as having "concern" (but for which there is no clearly accepted mandated action), is so far to the left on the distribution curve of cases that it is reached by up to 75% of all patients. This renders Category II useless as a screening test.

Electronic fetal monitoring (EFM) was introduced into practice in the late 1960's in an attempt to permit timely intervention (e.g., expedited delivery by cesarean delivery, use of vacuum or forceps, etc.) in situations in which the fetus appears to either be presently compromised already or will be so imminently. EFM has been widely adopted and used, for decades past and to the present, in the vast majority of births in the United States.

The premise of EFM is the recognition of asphyxia related to metabolic acidemia. The response to fetal heart rate (FHR) patterns is predicated on the identification and "rescue" of the asphyxiated fetus, hopefully, before it has suffered damage. Traditionally, when EFM data demonstrate an overall impression of "reassurance," labor is allowed to continue, with intervention being reserved for situations when EFM is abnormal, indicative of significant asphyxia (from metabolic acidosis), or an acute emergency arises (e.g., fetal bradycardia). Such interpretations are often very subjective; even distinguished experts often disagree as to the significance of individual patterns.

In an improvement of the conventional means for interpreting EFM data and improving fetal outcomes in labor and delivery, the inventor hereof discloses in U.S. Pat. No. 9,131,860 (the disclosure of which is incorporated herein by reference in its entirety) an apparatus for identifying the level of fetal risk during labor. The apparatus includes at least one computer operative to receive input signals indicative of at least FHR and maternal uterine activity in a patient, the at least one computer further operative (i) to determine from the FHR at least baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e). The at least one computer is further operative to (iii) receive user-inputs indicative of the presence in the patient of one or more antecedent clinical parameters which elevate the level of fetal risk during labor, and (iv) to determine at a given point in time during labor a present level of risk to the fetus which takes into account only: the total number of the one or more antecedent clinical parameters which elevate the level of fetal risk during labor; and the total number of the parameters (a) through (e) that each simultaneously, independently exhibit at least one of the non-reassuring characteristics at the given point in time during labor. This invention has been demonstrated to yield consistent assessment of EFM data and, consequently, consistent identification of fetuses at risk for neurological injury. This Fetal Reserve Index (FRI) provides a more meaningful alternative to ACOG's Category System. FRI combines various risk factors and the presence of increased uterine contractions during labor to produce a statistically significant prediction of fetal risk for cerebral palsy. FRI's indicators of risk are valid much earlier in the pathophysiology than ACOG's Category System. By identifying potential concerns earlier in the process, it has been shown that poor outcomes can be reduced by proper clinical intervention, as well as that the emergency CDR, overall emergency deliveries, and total CDR can actually be reduced.

In a further improvement of the conventional means for interpreting EFM data and improving fetal outcomes in labor and delivery, the inventor hereof discloses in Published International Application WO/2018/094398 an apparatus for identifying the level of fetal risk during labor, the apparatus comprising: at least one computer operative to receive input signals indicative of at least FHR and maternal uterine activity in a patient, the computer operative (i) to determine baseline FHR variability, FHR accelerations, and FHR decelerations, and (ii) to determine when each of at least (a) FHR, (b) baseline FHR variability, (c) FHR accelerations, (d) FHR decelerations, and (e) maternal uterine activity exhibit at least one non-reassuring characteristic from among a plurality of pre-defined non-reassuring characteristics for at least the parameters (a) through (e). The computer is further operative to (iii) receive user-inputs indicative of the presence in the patient of one or more (f) maternal risk factors, (g) obstetrical risk factors, and (h) fetal risk factors which elevate the level of fetal risk during labor, and (iv) to determine at a given point in time during labor a present level of risk to the fetus which takes into account only: the total number of the parameters (a) through (e) that are each simultaneously, independently exhibit at least one of the non-reassuring characteristics at the given point in time during labor, and the total number of the parameters (f) through (h) which are present. An output depicts in a single graphical user interface one or more of the parameters (a) through (h) over time during labor, and the appearance of which single graphical user interface includes indicia for indicating the determined present level of risk to the fetus at any given point in time during labor and signaling the need for possible intervention in labor. The disclosure of Published International Application WO/2018/094398 (correspondingly disclosed in Published U.S. Application 2019/0274618) is incorporated herein by reference in its entirety.

In a further approach, the inventor hereof analyzed data from both before and up to 1 hour after birth. It was found, surprisingly and unexpectedly (and in contrast to prevailing opinion), that the process of adaptation from fetal to neonatal circulation is very different than has generally been believed. Instead of a linear improvement in the acid/base balance, there is commonly a profound worsening for variable time periods. Using this dataset, FRI was able to distinguish by the last FRI score prior to delivery three separate groups of babies who were at low, intermediate, and high risk of developing metabolic acidosis (which is generally defined as a base excess value of ≤−12 mMol/L and is the generally accepted predicate of cerebral palsy from complications of labor). It was also found that the neonatal heart rate shows, in 85% of patients, a profound tachycardia with loss of reactivity and variability over the first 10 minutes or more. Had such a pattern been seen prenatally, it would have generally been considered Category III under ACOG's Category System. In part, these findings help explain the poor performance of ACOG's Category System, as the abnormalities occur when generally no one has been looking. Published International Application WO/2020/102524, discussing the foregoing, is incorporated herein by reference in its entirety.

While the foregoing advances hold promise for improved outcomes in labor and delivery, neurological injury to neonates in consequence of progressive hypoxia and acidemia continues and, therefore, remains a problem in need of further solutions.

SUMMARY OF THE DISCLOSURE

Acidosis, as reflected by the BE value, has generally been the closest approximation to determining risk for impairment although experience to date has been insufficient to create precise estimates of risk for any given fetus. Demonstrated herein is a correlation between FRI and BE scores within cervical dilatations and between adjoining cervical dilatation (CDx) groups. These correlations are sufficiently strong to justify consideration of the FRI as a proxy, especially within the same cervical dilatation. Combining the information available in FRI may permit an inference of the risk of acidosis at the beginning of the $2^{nd}$ stage and can also suggest when FSS might be considered. In sum, it is an improvement on CTG to predict acidosis and its sequelae.

Disclosed herein are methods for reducing the risk, and identifying the existence, of neurological injury to a human fetus during labor.

In one embodiment, there is disclosed a method for reducing the risk of neurological injury to a human fetus during labor, comprising the steps of:
identifying during labor the risk of neurological injury to a fetus by:
at a first period in time during the first stage of labor, conducting an analysis of fetal blood to determine at least a first base excess (BE) value for the fetus;
determining a multiple of the median for the BE value at the first period in time by dividing the BE value by the median BE value of a dataset comprising a population of fetal BE values established at the same period in time during the first stage of labor as the first period, wherein a risk of neurological injury to the fetus is indicated when the BE value is a predefined multiple of the median (MoM) BE value; and
treating the fetus for which the risk of neurological injury is indicated by the identification step, wherein the treatment step comprises intervening in labor to reduce or eliminate the risk of neurological injury to the fetus through any conventional therapeutic measures.

In one aspect, the first period in time during labor is characterized by a cervical dilatation of between 0-3 cm.

According to another embodiment, there is disclosed a method for reducing the risk of neurological injury to a human fetus during labor, comprising the steps of:
identifying during labor the risk of neurological injury to a fetus by:
at a first period in time during the first stage of labor, conducting an analysis of fetal blood to determine at least a first base excess (BE) value for the fetus, wherein a risk of neurological injury to the fetus is indicated when the BE value is ≤−5; and
treating the fetus for which the risk of neurological injury is indicated by the identification step, wherein the treatment step comprises intervening in labor to reduce or eliminate the risk of neurological injury to the fetus through any conventional therapeutic measures.

In one aspect, the first period in time during labor is characterized by a cervical dilatation of between 0-3 cm.

According to a further embodiment, there is disclosed a method for reducing the risk of neurological injury to a human fetus before or during labor, comprising the steps of:
(a) monitoring the fetus for at least a first set of concurrent clinical parameters indicative of a present level of risk for neurological injury to the fetus;
(b) determining at a first period in time before or during the first stage of labor a present level of risk to the fetus for neurological injury based on the first set of concurrent clinical parameters, wherein the determined present level of risk is expressed as a numerical value (FRI value);
(c) determining a multiple of the median (MoM) for the FRI value at the first period in time by dividing the FRI value by the median FRI value of a dataset comprising a population of FRI values established at the same period in time during or before the first stage of labor as the first period, wherein the risk for neurological injury is indicated when the MoM of the FRI value is a predefined multiple of the median FRI value; and
(d) treating the fetus for which the risk of neurological injury is indicated by the step (c), wherein the treatment step comprises intervening before or during labor to reduce or eliminate the risk of neurological injury to the fetus through any conventional therapeutic measures.

Per one feature, the first period in time is a period in time during labor that is characterized by a cervical dilatation of between 0-3 cm.

Per another feature, when the risk of neurological injury is indicated by the step (c), the method comprises the further step of conducting an analysis of fetal blood at at least a second period in time during the first stage of labor to determine at least a base excess (BE) value.

Per a further aspect, the step of conducting an analysis of fetal blood comprises conducting the analysis at a third period in time during the first stage of labor, the third period in time being later than the second point in time, and determining at least a base excess (BE) value for each of the second and third periods in time.

Per still another aspect, the first period in time during labor is characterized by a cervical dilatation of between 0-3 cm, and the second and third periods in time during labor are each characterized by a cervical dilatation of less than 10 cm.

According to yet another aspect, the first set of concurrent clinical parameters comprise (a) FHR, (b) baseline FHR variability, (c) FHR accelerations, (d) FHR decelerations, and (e) maternal uterine activity, and the step of determining the present level of risk to the child for neurological injury comprises determining whether each concurrent clinical parameter (a) through (e) independently exhibits at least one non-reassuring characteristic, and transforming the number of the concurrent clinical parameters (a) through (e) that simultaneously, independently exhibit at least one non-reassuring characteristic into an indication of the present level of risk to the fetus corresponding to the number of the parameters (a) through (e) that simultaneously, independently exhibit at least one non-reassuring characteristic.

According to a still further embodiment, there is disclosed a method for reducing the risk of neurological injury to a human fetus during labor, comprising the steps of:
identifying during labor the risk of neurological injury to a fetus by:
at a first period in time during the first stage of labor, conducting an analysis of fetal blood to determine at least a first base excess (BE) value for the fetus;
at second period in time during the first stage of labor, later than the first point in time, conducting an analysis of fetal blood to determine at least a second base excess (BE) value for the fetus;
determining a rate of drop from the first BE value to the at least second BE value, wherein a risk of neurological injury to the fetus is indicated when the rate of drop is greater than a predefined value; and
treating the fetus for which the risk of neurological injury is indicated by the identification step, wherein the treatment step comprises intervening in labor to reduce or eliminate the risk of neurological injury to the fetus through any conventional therapeutic measures.

Per one aspect, the first period in time during labor is characterized by a cervical dilatation of between 0-3 cm.

Per a further aspect, the second period in time during labor is characterized by a cervical dilatation of less than or equal to 10 cm.

According to another feature, the risk of neurological injury to the fetus is indicated when the rate of drop is 46% or greater.

According to yet another embodiment, there is disclosed a method for reducing the risk of neurological injury to a human fetus during labor, comprising the steps of:
identifying during labor the risk of neurological injury to a fetus by:
at a first period in time during the first stage of labor, conducting an analysis of fetal blood to determine at least a first base excess (BE) value for the fetus;
at second period in time during the first stage of labor, later than the first period in time, conducting an analysis of fetal blood to determine at least a second BE value for the fetus;
determining a rate of drop from for the first BE value to the second BE value;
determining a multiple of the median (MoM) for the rate of drop by dividing the rate of drop by the median rate of drop of a dataset comprising a population of rates of drop for fetal BE values established at the same periods in time during the first stage of labor as the first and second periods, wherein a risk of neurological injury to the fetus is indicated when the MoM for the rate of drop is a predefined multiple of the median rate of drop; and
treating the fetus for which the risk of neurological injury is indicated by the identification step, wherein the treatment step comprises intervening in labor to reduce or eliminate the risk of neurological injury to the fetus through any conventional therapeutic measures.

According to one aspect, the first period in time during labor is characterized by a cervical dilatation of between 0-3 cm.

Per yet another aspect, the second period in time during labor is characterized by a cervical dilatation of less than or equal to 10 cm.

According to a still further embodiment, there is disclosed a method for identifying the existence of neurological injury to a human fetus during or before labor, comprising the steps of:
(a) monitoring the fetus for at least a first set of concurrent clinical parameters indicative of a present level of risk for neurological injury to the fetus;
(b) determining at a first period in time during or before labor a present level of risk to the fetus for neurological injury based on the first set of concurrent clinical parameters, wherein the determined present level of risk is expressed as a numerical value (FRI value);
(c) determining at a second period in time during or before labor, later than the first period in time, a present level of risk to the fetus for neurological injury based on the first set of concurrent clinical parameters, wherein the determined present level of risk is expressed as a FRI value;
(d) determining a rate of drop from the first FRI value to the second FRI value;
(e) determining a multiple of the median (MoM) for the FRI value at the first period in time by dividing the FRI value by the median FRI value of a dataset comprising a population of FRI values established at the same period in time during or before the first stage of labor as the first period, wherein the risk for neurological injury is indicated when the MoM of the FRI value is a predefined multiple of the median FRI value; and
(f) determining a MoM for the rate of drop by dividing the rate of drop by the median rate of drop of a dataset comprising a population of rates of drop for FRI values established at the same periods in time during or before the first stage of labor as the first and second periods, wherein the existence of neurological injury to the fetus is indicated when the MoM for the rate of drop is a predefined MoM rate of drop.

Per one feature, the first set of concurrent clinical parameters comprise (a) FHR, (b) baseline FHR variability, (c) FHR accelerations, (d) FHR decelerations, and (e) maternal uterine activity, and the step of determining the present level of risk to the child for neurological injury comprises determining whether each concurrent clinical parameter (a) through (e) independently exhibits at least one non-reassuring characteristic, and transforming the number of the concurrent clinical parameters (a) through (e) that simultaneously, independently exhibit at least one non-reassuring characteristic into an indication of the present level of risk to the fetus corresponding to the number of the parameters (a) through (e) that simultaneously, independently exhibit at least one non-reassuring characteristic.

Per another feature, n the second period of time is up to an hour later than the first period of time.

According to still another feature, when the risk of neurological injury is indicated by the step (b) and/or the step (c), the method comprises the further step of conducting an analysis of fetal blood at at least a third period in time during or before the first stage of labor to determine at least a base excess (BE) value.

In another embodiment, there is disclosed a method for reducing the risk of neurological injury to a human fetus during labor, comprising the steps of:
(a) monitoring the fetus for at least a first set of concurrent clinical parameters indicative of a present level of risk for neurological injury to the fetus;
(b) determining at a first period in time during or before labor a present level of risk to the fetus for neurological injury based on the first set of concurrent clinical parameters, wherein the determined present level of risk is expressed as a numerical value (FRI value);
(c) determining at a second period in time during or before labor, later than the first period in time, a present level of risk to the fetus for neurological injury based on the first set of concurrent clinical parameters, wherein the determined present level of risk is expressed as a FRI value;
(d) determining a rate of drop from the first FRI value to the second FRI value, wherein a risk of neurological injury to the fetus is indicated when the rate of drop is greater than a predefined value; and
treating the fetus for which the risk of neurological injury is indicated by the identification step, wherein the treatment step comprises intervening in labor to reduce or eliminate the risk of neurological injury to the fetus through any conventional therapeutic measures.

Per one feature, the first period in time during labor is characterized by a cervical dilatation of between 0-3 cm.

According to a further feature, the second period in time during labor is characterized by a cervical dilatation of less than or equal to 10 cm.

According to still another feature, the risk of neurological injury to the fetus is indicated when the rate of drop is 46% or greater.

Also disclosed are apparatus for carrying out the methods of this disclosure.

BRIEF DESCRIPTION OF THE DRAWINGS

The present invention will be appreciated from the following description and accompanying drawings, of which:

FIG. 7 is a table summarizing logistic regression analyses for predicting membership in the bottom 30% of BE scores at the beginning of Stage 2 of labor.

FIG. 8 is a table summarizing logistic regression analyses for predicting membership in the bottom 30% of pH readings at the beginning of Stage 2 of labor.

DETAILED DESCRIPTION

Figure 1:
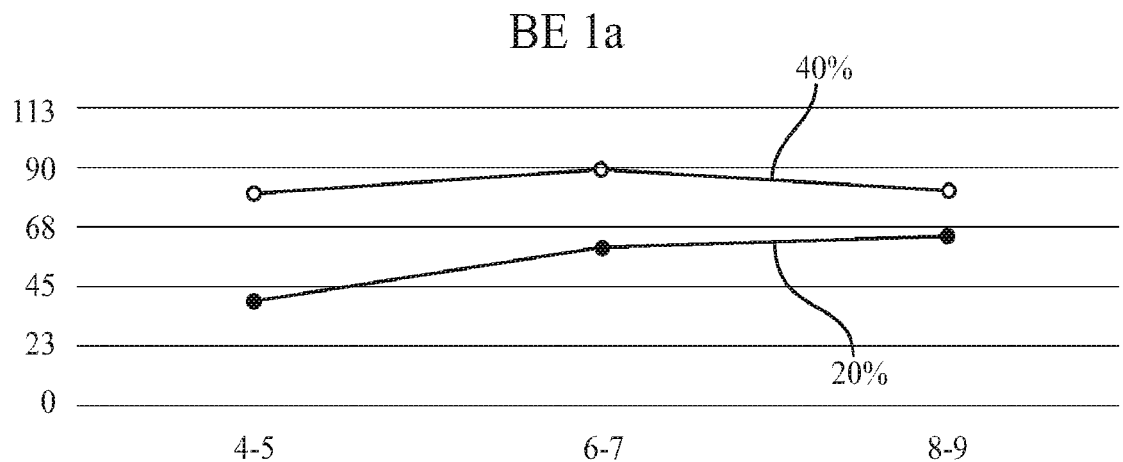
FIG. 1 graphically depicts the sensitivity for detection of reaching BE values below −12 mMol/L at various cervical dilatations, taken from data for a population of babies.

Methods and apparatus for reducing the risk of neurological injury to a human fetus during labor are described below. These methods and apparatus are premised on the analysis, described below, of a dataset of fetal scalp samples, all taken in the first stage of labor. More specifically, this analysis involved the transformation of certain results to non-parametric "multiples of the median" (MoMs). By using MoMs, the degree of deviancy from the median at discreet points—identified here as the amount of cervical dilatation at a specific time—serves as the independent variable to predict the likelihood of risk for neurological damage.

As required, detailed embodiments of the present invention are disclosed herein. However, it is to be understood that the disclosed embodiments are merely exemplary of the invention that may be embodied in various and alternative forms. The accompanying drawings are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

As used herein, "child" is intended to comprehend the human child both prior to delivery (i.e., the child as a fetus) and subsequent to delivery (i.e., the neonatal child). The terms "fetus" and "child as a fetus" are used interchangeably, as are the terms "neonate" and "neonatal child." In context, "child" also refers to the child as a fetus and as a neonate.

"Base excess" (BE) as used herein refers to the amount of base or acid that would have to be added to one liter of the neonate's blood to restore it to a physiological level of 7.4 at a pCO2 of 40 mmHg at 98.6° F. (37° C.). A lower than average BE is non-reassuring, and a value of ≤−12 mMol/L is considered to be at high risk for neurological damage.

"Computer" as used herein means and refers to a device that can store, retrieve, and process data, and includes any of a general purpose computer, a handheld computing device (e.g., a smartphone, tablet computer, laptop computer, etc.), and/or a special purpose computer.

Fetal Monitoring

In the exemplary embodiments of the invention described herein, the patient is monitored during labor for at least a first set of parameters that are employed to establish a level of risk for neurological injury to the child. These parameters comprise a plurality of variable, dynamic parameters associated with EFM, including (a) baseline FHR, (b) baseline FHR variability, (c) FHR accelerations, and (d) FHR deceleration. Optionally, these parameters also include a dynamic parameter (e) maternal uterine activity (i.e., uterine contractions) associated with intrauterine activity ("IUA"). In this context, the monitored patient refers to the mother and/or the fetus, as appropriate to the monitored parameters. In the exemplary embodiment, these parameters, as monitored, are assessed for assurance or non-reassurance according to the characteristics set forth in Table 1 below.

TABLE 1

EFM and IUA Variables

| | Reassuring | Non-Reassuring (Point A) |
|---|---|---|
| Uterine contractions | ≤8/20 Minutes | >8/20 Mins |
| FHR baseline variability | 5-25 BPM | <5 or ≥15 BPM |
| FHR accelerations | >15 × 15 BPM/15 Secs | <15 BPM/15 Secs |
| FHR decelerations | No late return to baseline | Late return to baseline (ie. + OCT) |
| Baseline FHR (BPM) | 110-160 BPM | >15 BPM Rise since admission (<160) |

Optionally, the monitored parameters may also include certain additional maternal, obstetrical, and fetal risks ("MOFR") factors (separate from EFM variables), as follows: (f) Maternal risk factors, (g) Obstetrical risk factors, and (h) Fetal risk factors (separate from EFM). Per this example, the parameter (f) of "Maternal Risk Factors" comprehends the following non-reassuring characteristics:

1) Decreased cardiac output/vascular perfusion of the placenta
   a. Cardiac Disease with risk of decreased cardiac output in pregnancy
   b. Hypertension (Chronic and Pregnancy induced)
   c. SLE (systemic lupus erythematosus), etc.
2) Oxygen carrying capacity
   a. Pulmonary disorders (e.g. Asthma)
   b. Anemia and Hemoglobinopathy
3) Infection (chronic and acute)
4) Chronic debilitating disease
5) Malabsorption/Poor weight gain
6) Endocrine—Diabetes and Thyroid disorders
7) Advanced maternal age
8) Drug abuse, addiction, and smoking
9) Obesity—BMI (body mass index)>35
10) Short stature (≤5'2")
11) Epidural anesthesia Per this example, the parameter (g) of "Obstetrical Risk Factors" comprehends the following non-reassuring characteristics:

1) IUGR (intrauterine growth restrictions)/Macrosomia
2) Oligohydramnios
3) Polyhydramnios
4) Bleeding and abruption
5) Previous cesarean section
6) Placental and umbilical cord anomalies
7) Rupture of membranes (PPROM—preterm or premature rupture of membranes, SROM—spontaneous rupture of membranes, AROM—artificial rupture of membranes)
8) Dystocia (protraction and arrest disorders of labor)
9) Malpresentation Finally, per this example, the parameter (h) of "Fetal Risk Factors" comprehends the following non-reassuring characteristics:

1) Abnormal Dopplers/BPP (biophysical profile)
2) Genetic disorders
3) Fetal arrhythmia
4) Meconium passage
5) Chorioamnionitis
6) Second stage of labor—pushing
7) Amnioinfusion
8) Discontinuation of Pitocin due to fetal intolerance
9) Conversion patterns (acute prolonged tachycardia (>170 bpm))
10) Ominous overshoots
11) Bradycardia (<100 bpm)
12) Missing important data in labor (e.g. lack of EFM in second stage)

Interpretation of the various parameters described above may be done per convention, including, optionally, using the methodology disclosed by the inventor hereof in U.S. Pat. No. 9,131,860 and Published U.S. Application 2019/0274618. More particularly according to one embodiment disclosed in those references, the method most generally comprises determining whether each monitored or evaluated parameter independently exhibits at least one non-reassuring characteristic, such as, for instance, the non-reassuring characteristics discussed above; and deriving an indication, referred to as the "Fetal Reserve Index" (FRI) score, of the present level of risk corresponding to the number of these parameters which simultaneously, independently exhibit at least one non-reassuring characteristic/are present. Per that exemplary methodology, the number of parameters that simultaneously, independently exhibit at least one non-reassuring characteristic, on the one hand, and the indication of the present level of risk for neurological injury, on the other hand, is directly related. Thus, for instance, the highest level of risk for neurological injury according to the method wherein the parameters (a) through (e) are monitored corresponds to the simultaneous, independent exhibition of at least one non-reassuring characteristic for/presence in the patient of each of the parameters (a) through (e), while the lowest level of risk to of neurological injury corresponds to the absence of any exhibited non-reassuring characteristics for/presence in the patient of any of these parameters.

It will be appreciated that the parameters (a) through (e) are dynamic parameters; that is, they are subject to change in either direction (e.g., from normal, or reassuring, to abnormal, or non-reassuring, and back again) during the course of monitoring. On the other hand, the MOFR parameters (f) through (h) are unidirectional in nature; that is, once (and if) they occur (whether during the course of labor or even before), they negatively affect the FRI score. It will also be appreciated that the occurrence of a non-reassuring characteristic for each parameter (f) through (h) is, per the exemplary embodiment, sufficient to negatively affect the FRI score. It is unnecessary, for instance, that the parameter (f) of "Maternal Risk Factors" display more than one of the eleven exemplary non-reassuring characteristics listed above.

"Simultaneous" in the context of this disclosure means at the exact same or, at least, at the point in time during labor when the determination of assurance/non-reassurance for each monitored parameter overlaps. In an exemplary embodiment, this assessment of risk is made in 20-minute intervals coinciding with the determination of assurance/non-reassurance for the IUA parameter (e).

"Independent" in the context of this disclosure means that the exhibition/non-exhibition of one or more non-reassuring characteristics by each monitored parameter affects the determination of the present level of risk without regard to the exhibition/non-exhibition of one or more non-reassuring characteristics by any other monitored parameters. That is, while the exhibition/non-exhibition of each monitored parameter will collectively affect the determined present level of risk, each monitored parameter is considered independently of the others in respect of displaying reassuring/non-reassuring characteristics.

The FRI score is derived as follows: Each of the monitored parameters (e.g. (a) through (h)) is assigned a first numerical value (e.g., "1") if the parameter was deemed normal (i.e., reassuring) and a second numerical value (e.g., "0") if abnormal (i.e., non-reassuring). The first and second numerical values are the same for each parameter. That is, only two values are employed (e.g., a 1 or a 0). The FRI score per this example is calculated on the number of points divided by the number of parameters involved (e.g., 5) and multiplied by 100 to give a percentage. As an example, a total of 5 monitored parameters ((a) through (e)) would yield a FRI score calculated as the number of points divided by 5 and multiplied by 100 to give a percentage. A total of 5 parameters ((a) through (e)) being normal would result in a FRI score of 100% (5/5), whereas a loss in points—as a function of the presence of abnormal or non-reassuring characteristics for any of the monitored FRI parameters (a) through (e)—would result in an FRI score of 80% (4/5), 60% (3/5), 40% (2/5), 20% (1/5), and 0% (0/5). Alternatively, a total of 8 parameters ((a) through (h)) being normal would result in a FRI score of 100 (8/8), whereas a loss in points—as a function of the presence of abnormal or non-reassuring characteristics for any of the monitored FRI parameters (a) through (h)—would result in an FRI score of 100% (8/8), 87.5% (7/8), 75.0% (6/8), 62.5% (5/8), 50.0% (4/8), 37.5% (3/8). 25.0% (2/8), 12.5% (1/8) and 0% (0/8).

Identification of the present level of risk for neurological injury is made by considering each parameter, when present, independently from the other parameters. Thus, the schemes for identifying a present level of risk that are within the scope of this invention are not, as is the case with some conventional methodologies, the consequence of interdependence between any parameters but, rather, are strictly a function of the number of parameters which are present in a patient and/or simultaneously, but independently, non-reassuring in their exhibited characteristics. Consistent with the foregoing, this methodology is also distinguished in that it does not take into account the degree of non-reassurance indicated by the one or more characteristics of any monitored parameters. Rather, the parameters are preferably weighted equally so that any exhibition of non-reassurance according to the predetermined non-reassuring characteristic(s) for the parameters (e.g., (a) through (e) or (a) through (h)) will cause each such parameter to contribute equally to the presently identified level of risk.

It is also contemplated by the exemplary embodiments that the method of the present invention comprehends assigning a predefined risk category to the child, wherein the predefined risk category corresponds to the determined present level of risk. For instance, the present level of risk for neurological injury may be identified both by a specific FRI score, as discussed above, and/or a grade for easy interpretation. For example, and without limitation, the "grade" of an example takes the form of arbitrary color zones, akin to traffic lights. In the example of this disclosure, the lowest level of present risk is identified as the "green zone" and comprehends FRI scores >50%. An increased (relative to the lowest level) level of present risk to the fetus is identified as the "yellow zone" and comprehends FRI scores ≤50%, and >26%. The highest level of present risk is identified as the "red zone" and comprehends FRI scores ≤25%. The lower the score, the greater the risk of acidosis and adverse outcome.

Experimental Data

From a dataset of FHR tracings and BE values from fetal scalp samples, all taken in the first stage of labor, Fetal Reserve Index (FRI) scores were derived and analyzed along with BE measurements at corresponding times during labor. Using the available measurements of this dataset, FRI scores were calculated as described above and in the disclosures of U.S. Pat. No. 9,131,860, Published International Application WO/2020/102524, and Published International Application WO/2018/094398. The evaluation of historic fetal and neonatal data corresponding to various parameters (e.g., FHR, NHR, pH, Base Excess, etc.) validates the inventor's hypothesis, as well as the utility of the present invention in reducing the risk of neurological injury to the fetus.

Still more particularly, data from 475 records of high-risk, term singleton pregnancies were used to assess the relationship between FRI and the EFM tracing, the course of labor, and the neonatal outcome in the first hour of life. These data were collected in the 1970s, mostly at the University of Southern California—LA County Hospital and some at Yale New Haven Hospital. Each case was supervised by an attending MFM faculty physician. The monitoring strips had 5 data lines (EFM, contraction pattern, expanded variability tracing, maternal respirations, and maternal heart rate). After delivery, the analysis continued with continuous neonatal heart rate (NHR), respirations, ECG, and indwelling catheter for blood pressure, pH, and umbilical artery core blood (CB) BE and pO2. Contemporaneous annotations were provided along the entire record for scalp sampling, its results (e.g. pH, Base Excess, pO2), blood pressures, drugs administered, anesthesia provided, and other relevant data. Prenatally, scalp sampling was done as indicated and recorded on the monitor strips. Postnatally, cord gases were routinely obtained at 1, 4, 8, 16, 32, and 64 minutes. Neonatal observations included: 1- and 5-min Apgar scores, NHR with time to return to predelivery rate and reactivity, and umbilical artery pH, BE, and pO2. The majority of these records had all of the foregoing measurements.

All monitoring began, in the presence of rupture of membranes, with fetal scalp electrodes (FSE) and intrauterine pressure catheter (IUPC) in place. NHR was recorded continuously—similar to intrapartum FHR.

The results of FRI scoring were divided into three groups for purposes of further analysis. As discussed above, the lowest level of risk is identified as the "green zone" and comprehends FRI scores >50%; an increased (relative to the lowest level) level of present risk to the fetus is identified as the "yellow zone" and comprehends FRI scores ≤50% and >26%; and the highest level risk is identified as the "red zone" and comprehends FRI scores ≤25%. Approximately 10% of cases in the evaluated records were in the red zone, 30% were yellow, while 60% were in the green zone. Table 2, below, summarizes the relevant characteristics of the above-described sample population.

TABLE 2

| | Mean (sd) Median | Descriptive Distributions |
|---|---|---|
| Maternal age | 23.63 (5.88) 22.00 | |
| Gestational Age | 39.51 (2.16) 40.00 | |
| Weight in Grams | 3275.40 (539.48) 3300 | |
| % of patients assessed as being in different FRI risk categories at 1 hour after admission | | Red −.250) = 48 (10%) Yellow (.375-.500) = 142 (30%) Green (.625-1.0) = (60%) |
| APGAR1 | 7.84 (1.89) 9.00 | |
| APGAR5 | 8.76 (1.13) 9.00 | |
| Bottom 30% of BE scores at the beginning of the second stage of labor | | N = 196 LE-9 = 59 (30%) GT-9 = 137 (70%) |

It has been determined from these data that both the FRI scores and BE values worsen (i.e., go down) as labor progresses and the fetus is exposed to more stress. On this basis, the inventor hereof demonstrated that a given measurement taken early in labor could have very different implications than the same measurement taken later; e.g., in the second stage.

These data were analyzed by their actual measurements—e.g., the BE values per se—as well as by means and standard deviations thereof. They were also transformed to non-parametric "multiples of the median" (MoMs), as opposed to parametric means and standard deviations. By using MoMs, the degree of deviancy from the median at discreet points—identified here as the amount of cervical dilatation at a specific time—serves as the independent variable to predict the likelihood of the cord blood BE being ≤−12 mMol/L (the definition of the risk for metabolic acidosis). According to this measure, a BE of −7 at 4 cm dilatation would likely have a greater chance of getting below −12BE mMol/L by the end of pregnancy or in cord blood than would the same −7BE mMol/L reading at 10 cm dilatation (i.e., in the $2^{nd}$ stage of labor). The actual measurements from these data bear out this conclusion.

Analysis of the data demonstrates that average fetal scalp sample (FSS) BE and pH values (both medians and means) decreased gradually over the course of the $1^{st}$ stage with an approximately linear slope (p<0.000 for an ANOVA test of mean differences and the significance of the linear component). As cervical dilatation increases, the medians for both BE and pH decline. The fall of BE and pH during the 1st stage of labor typically begins gradually and becomes more rapid as full dilatation approaches. The drop accelerates through delivery until after birth four minutes postnatally A more detailed discussion of the results of the foregoing analysis follows:

Referring to FIG. 1, there is shown a graph depicting the percentage of BE values below −12 mMol/L at cervical dilatations of each of 4-5 cm, 6-7 cm, and 8-9 cm for specific populations from the dataset. Specifically, the bottom line plots these results for the population of babies from the dataset who screened positive for metabolic acidosis at a rate of 20%, while the top line plots these results for the population of babies from the dataset who screened positive for metabolic acidosis at a rate of 40%. As shown, at 4-5 cm dilatation, 40% of babies from the 20% screen-positive population showed BE values below −12 mMol/L, while 80% of babies from the 40% screen-positive population showed such scores. For the 20% screen-positive population, the percentage increased to about 60% at 8-9 cm dilatation. For the 40% screen-positive population, the percentage was approximately 80% at the same time.

Figure 2:
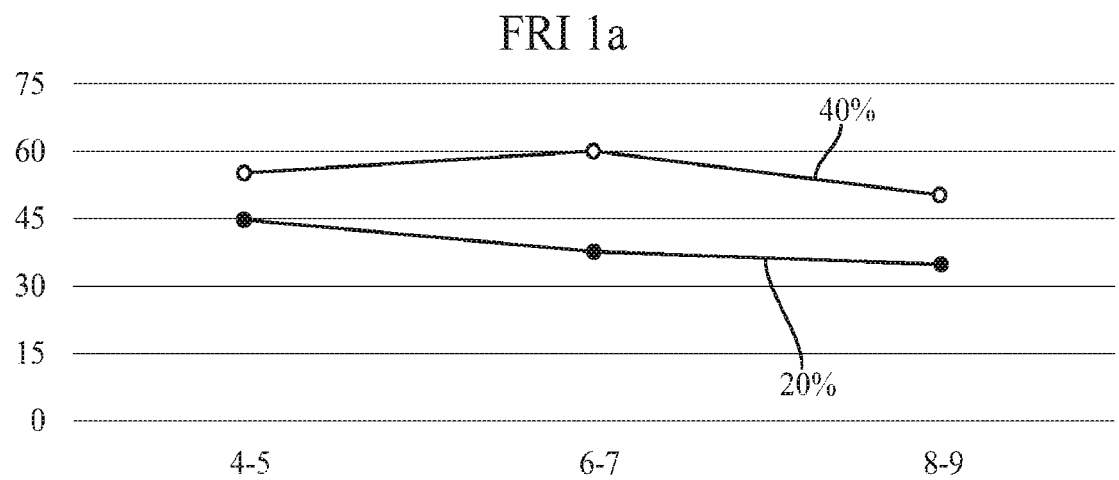
FIG. 2 graphically depicts the FRI scores, taken from the same data and at the same cervical dilatations, as in FIG. 1.

Referring next to FIG. 2, the same datasets from FIG. 1 were analyzed at the same cervical dilatations (i.e., 4-5 cm, 6-7 cm, 8-9 cm), using the calculated FRI scores for the babies instead of the BE values. In this graph, the bottom line plots these results for the population of babies from the dataset who screened positive for metabolic acidosis at a rate of 20%, while the top line plots these results for the population of babies from the dataset who screened positive for metabolic acidosis at a rate of 40%. The FRI scores performed in parallel, although not quite as well, as the BE results (which is a direct measurement of fetal acidosis, as opposed to the FRI, which is an indirect predictor of it).

Figure 3:
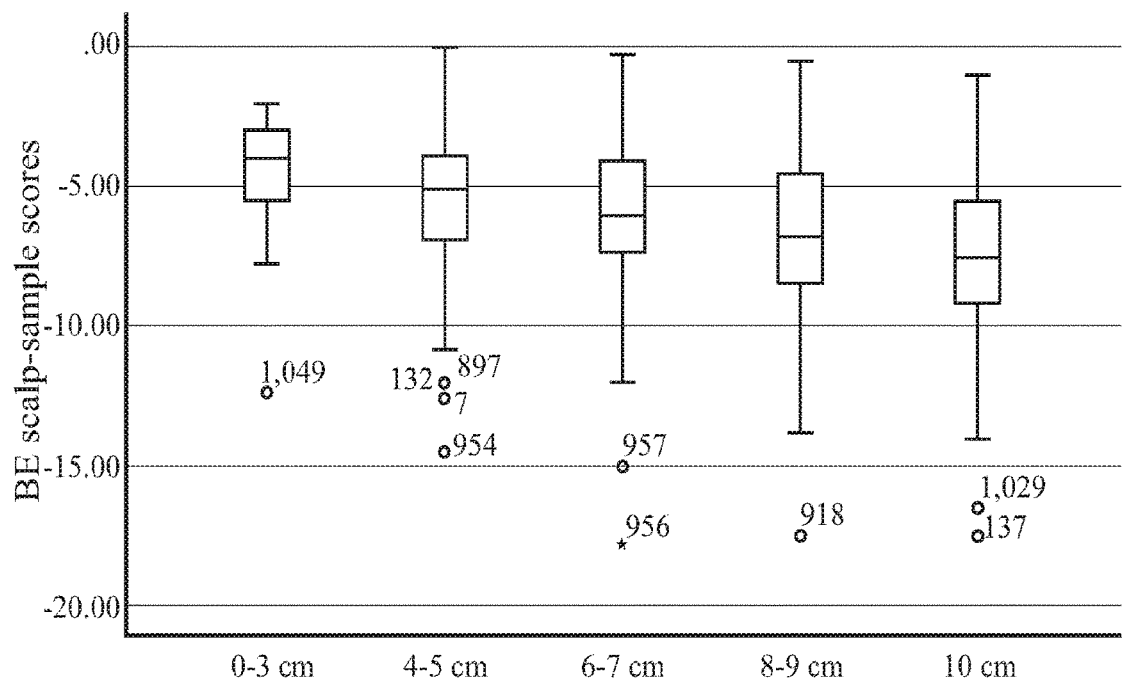
FIG. 3 graphically (box plots) plots the decline in BE values and FRI scores over the first stage of labor.

Referring now to FIG. 3, the decline in BE and FRI scores over the $1^{st}$ stage of labor (i.e., between 0 and 10 cm cervical dilatation) was evaluated. The "box plots" of FIG. 3 show the middle 50% of scores with brackets around them representing the $99^{th}$ percentiles. A few outliers can be seen on some categories of dilatation. These data show that there is a gradually increasing acidosis in the fetus during labor—presumably as the fetus is exposed to contractions over time.

The foregoing data were then converted from parametric means and standard deviations to MoMs for each dilatation cohort. Since the baseline is moving with dilatation, the MoM of any given BE measurement is different based upon the dilatation. However, this allows a standardized interpretation, as a function of the MoM value, without having to constantly adjust by hand for the dilatation.

The MoM score reflects the progression downward (i.e. MoMs increase as the score gets worse).

It is notable that the raw BE value is a negative number. Since the FRI score is positive, the results given herein arbitrarily use positive numbers for the BE MoMs. It would otherwise be very confusing to have the MoMs (FRI and BE) going in different directions. Furthermore, for most clinicians it is easier to visualize the significance of differences in numbers greater than 1 as opposed to negative numbers.

TABLE 3

MoM Conversion of Fetal Scalp BE Scores

| Dilatation Raw BE Scores | 0-3 cm MoMs | 4-5 cm MoMs | 6-7 cm MoMs | 8-9 cm MoMs | 10 cm MoMs |
|---|---|---|---|---|---|
| −2 | 0.5 | 0.4 | 0.3 | 0.3 | 0.3 |
| −4 | 1.0 | 0.8 | 0.7 | 0.6 | 0.5 |
| −6 | 1.5 | 1.2 | 1.0 | 1.0 | 0.8 |
| −8 | 2.0 | 1.6 | 1.3 | 1.2 | 1.1 |
| −10 | 2.5 | 2.0 | 1.7 | 1.5 | 1.3 |
| −12 | 3.0 | 2.4 | 2.0 | 1.8 | 1.6 |
| −14 | 3.5 | 2.8 | 2.3 | 2.1 | 1.9 |

As can be discerned from Table 3, above, at earlier dilatations (e.g., 0-3 cm) a raw value of −8 (left column) is close to twice (negative) the median score (2.0 MoM), so that the risk implied by such a value is relatively high. On the other hand, later in the course of delivery, a raw BE value of −8 would be "normal" in the sense of being very close to the median score (1.1MoM).

Figure 4:
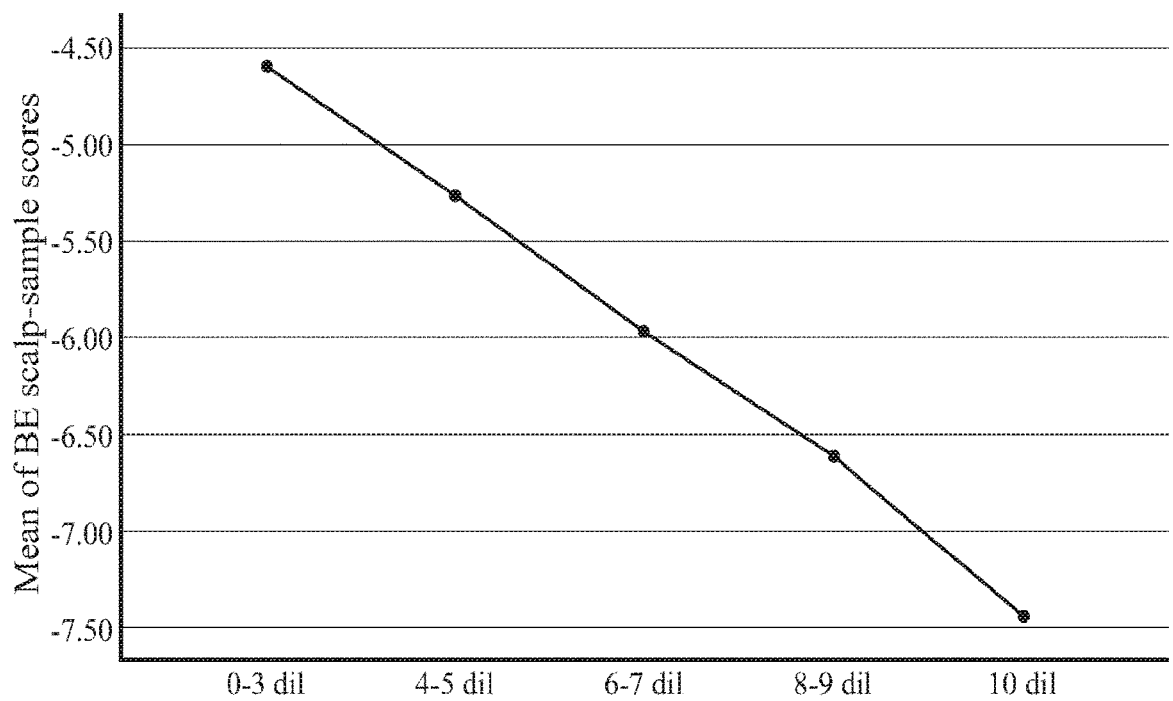
FIG. 4 plots the reduction in median BE values over the first stage of labor.

Using the median comparisons, there is a 46% drop in BE from 0-3 cm to 10 cm dilatation. The reduction for the means is very similar and linear, with a proportionate reduction of 38%. See FIG. 4.

Using the proportionate BE median drop of 46% between cervical dilatations from 0-3 cm to 10 cm (see Table 3), a simple equation, $X=(0.46)(-12)$, indicates that BE values of −5.52 or greater at a cervical dilatation of 0-3 cm will, on average, have a high risk of reaching a BE of $\leq -12$ at birth.

The corresponding figure derived from the drop in means suggests that, with a BE value of at least −4.56 or worse at a cervical dilatation of 0-3 cm, the average BE value will reach down to −12 at birth.

This new score (hereinafter referred to as the "Initial Drop Rate," (IDR) or "Initial Drop Trajectory") will aid in providing an early warning of the risk of acidemia at birth (operationalized as having a cord gas reading of −12 mMol/L BE at birth). In this analysis, the first scalp sample readings (BE1) and the proportionate reduction in BE from the first to the second scalp sample reading (BE_drop_1_2) are used as the variables of interest. Table 4, below, presents the logistic regression output:

TABLE 4

Logistic Regression Results for BE variables

| | B* | Sig | Exp(B) | Lower 95% CI for Exp(B) | Upper 95% CI for Exp(B) |
|---|---|---|---|---|---|
| BE1 | −.61 | <.000 | .55 | .46 | .65 |
| BE_drop_1_2 | .65 | <.000 | 1.92 | 1.34 | 2.74 |
| Constant | −5.95 | <.000 | .003 | | |

Logistic regression focuses on the logit, the natural logarithm of the odds of an outcome, occurring (here, the odds of being exposed to acidemia risk at birth). The B (beta) represents the amount of change in the logit for a one-unit change in the predictor variable. The constant represents the log odds of acidemia if both of the predictor variables were =0.

In Table 4, the Exp(B)'s are the B's transformed into odds ratios with the other variables in the regression equation held constant. Odds ratios less than 1 indicate that outcomes are becoming less likely as the predictor increases, while odds ratios greater than 1 indicate that the outcome is becoming more likely as the predictor increases.

Table 4 demonstrates that both the starting BE level and its trajectory as reflected by the drop in BE levels from the first to the second reading are very important in predicting acidemia risk at birth: As BE values become more negative, the chances that the fetus will experience acidemia risk at birth are increased; similarly, with the initial level of BE controlled, the greater the rate of decline between the first and second scalp sampling of BE, the greater the risk of acidemia at birth. These findings can be represented graphically, as shown in FIG. 5.

Figure 5:
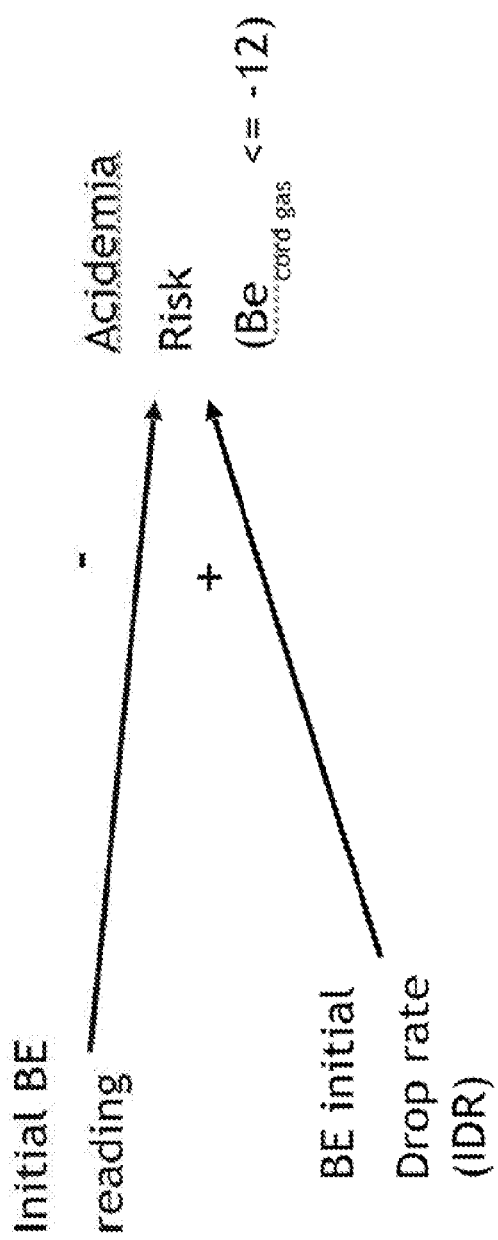
FIG. 5 is a diagrammatic depiction of a model showing the significance of the variables of initial BE value and the rate of drop thereof in relation to the risk of acidemia.

The model, summarized in FIG. 5, is useful for visualizing the nature of the influence of the variables considered important enough to be in the model. As a whole, the model may be evaluated both empirically and conceptually. From an empirical standpoint, the Hosmer-Lemeshow test (if it is significant) lets us know if there are really important things being left out of the equation. Here it is significant (<0.02)—suggesting that the model is mis-specified and that examining the model from a clinical and theoretical eye should be fruitful.

The second empirical method is to look at the analog to the R square, known as the Nagelkerke R Square. Its value is 0.32, suggesting that about a third of the variance in dichotomized BE values at birth (acidemia risk) can be explained by these two variables alone. Internally, both of the variables (BE1 and the drop from BE1 to BE2 as a proportion) are highly significant.

These empirical results can be further investigated in a couple of ways. One is to look at the summary classification table, reproduced below in Table 4.

TABLE 4

Classification Table for MoM-converted FRI and BE Scalp Sample Readings on Acidosis Risk at Birth

| | Observed Abnormal BE ($\leq -12$ ml/l) | Observed Normal BE (>−12 ml/l) | |
|---|---|---|---|
| Regression Estimated Abnormal BE | 17 | 7 | 24 |
| Regression Estimated Normal BE | 37 | 276 | 313 |
| | 54 | 283 | 337 |

In Table 4, "sensitivity" (true positives/(true positives+false negatives) is 32%; "specificity" (true negatives/(true negatives+false positives) is 98%; the "Positive Likelihood Ratio" (Sensitivity/1−Specificity) is 23 [this a single-statistic measure using the coordinates of a ROC (Receiver Operating Characteristic) curve—and the equation differentiates enormously between true and false positives]; the "Negative Likelihood Ratio" (1−Sensitivity/Specificity) is 0.70; the PPV (true positives/all cases tested as being positive) is 81%; NPV (true negatives/all cases tested as negative) is 88%; and accuracy=(true positives and true negatives)/total is 88%.

Notably, both PPV and NPV have to be interpreted with caution in samples that do not accurately reflect the population distributions. If the incidence of an outcome is higher than the population, the PPV will be higher than can be expected in practice.

Figure 6:
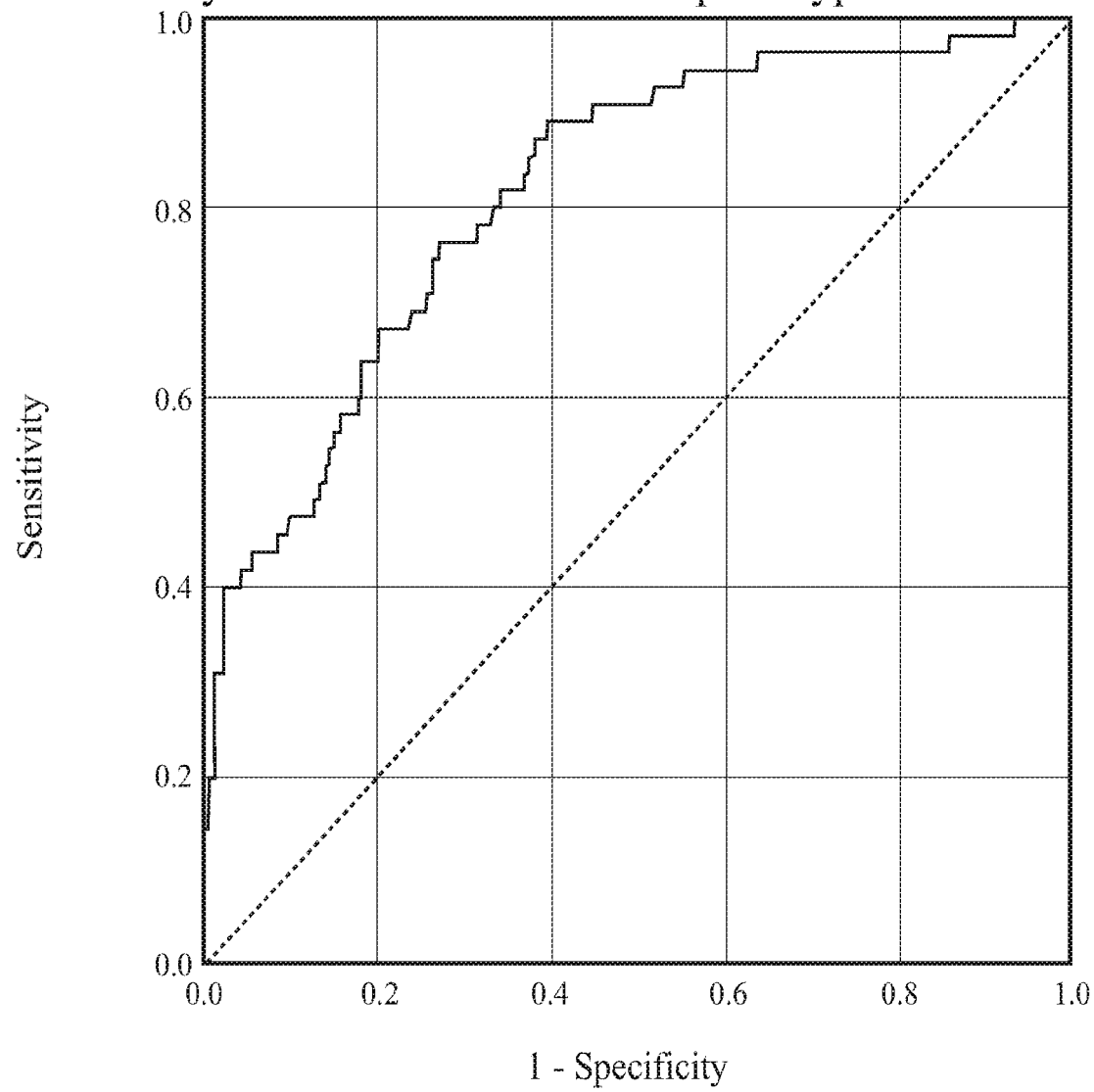
FIG. 6 compares the sensitivity and specificity of previously derived initial BE values and the BE rate of drop, in association with an ROC analysis.

Referring next to FIG. 6, the foregoing results are compared using a ROC curve analysis. This is accomplished by saving the predicted probabilities from the logistic regression analysis and using them as the predictor in the ROC analysis. The area under the curve is 0.82 (significance <0.000), reflecting the facts that early BE readings, as well as the rate at which these readings are falling as birth approaches, are important contributors to the prediction of acidemia risk at birth.

The correlation between untransformed FRI and BE scores within cervical dilatations and between adjoining C×D groups was also computed. The results are shown in Table 5 below. In Table 5, the following marks indicate level of significance: ^=<0.05; *=<0.01;=<0.001;*=<0.000 These correlations are sufficiently strong to justify consideration of the FRI as a proxy, especially within the same cervical dilatation. There is a modest upward trend in association between FRI and both BE and pH later in the $1^{st}$ stage, suggesting that as change begins to occur, the variation in scores increases.

the reading at 6-7 cm versus 4-5 cm, the R is 0.50 (p<0.007). The $FRI_{4-5\ cm}$ coefficient approaches significance (<0.099), but the FRI drop between two successive ranges is highly significant (p<0.002). Similarly, we predict the extent of BE drop can be a management tool, per se. The coefficient for $FRI_{4-5\ cm}$ does not reach significance (Beta=0.10, p<0.526), but the FRI trajectory is highly significant (Beta=−0.48, p<0.005).

35 cases had FSS at both 6-7 cm and 8-9 cm. Replicating this analysis, the corresponding drop and starting FRI variables together generate a multiple R of 0.69. The starting level at 6-7 cm and the drop between 6-7 cm and 8-9 cm are highly significant. Both the correlations and regression analyses aimed at predicting BE contemporaneously are compatible.

Having shown successful prediction of levels of BE within and across adjoining cervical dilatations, the relationship of $1^{st}$ stage FRI scores (both level and trajectory) and the risk of being in the bottom 30% of BE scores at the beginning of the 2nd stage was assessed. Using logistic regression equations, two sources of information drawn from cervical dilatations 5 to 7 cm were analyzed. FIG. 7 shows these results for BE; FIG. 8 shows these results for pH. In summary, between cervical dilatations of 4 and 10, the drop is 50%; it is 41% for a cervical dilatation of 5; and 27% for cervical dilatations of 6 and 7. In each comparison, a few cases actually improve (~10%).

TABLE 5

|  | 4 cm | 5 cm | 6 cm | 7 cm | 8 cm | 9 cm | 10 cm |
| --- | --- | --- | --- | --- | --- | --- | --- |
| Correlation between FRI and BE |  | .31** | .39*** | .33^ | .51** | .58** | 49*** |
| Correlation between FRI and pH | .36** | .34*** | .36*** | .34^ | .61** | .08 | 40*** |
| Correlation between FRI and BE at the next CX dilatation (ex: FRI4-BE5) | .18 | .10 | .33 | .67** | .32 | .00 |  |
| Correlation between FRI and pH at the next CX dilatation (ex: FRI4-pH5) | .22 | .38^ | .39 | .72** | .51 | −.27 |  |

These associations improve using multiple regressions to embrace information regarding both FRI level and its trajectory from the previous time period. Table 6, below, shows BE results regressed on FRI and FRI Drop within grouped cervical dilatations. Four analyses are presented in this table. Row 1 analyses the level of BE at 6-7 cm dilatation; row 2 analyzes the drop in BE at two point, a cervical dilatation of 4-5 cm to a cervical dilatation of 6-7 cm; and the next two rows replicate this analysis for BE at 8-9 cm and the drop in BE between 6-7 cm to 8-9 cm dilatation.

TABLE 6

|  | Multiple R (sig) | $FRI_{4-5}$ Beta (sig) | FRI drop$_{4-5 to 6-7}$ Beta (sig) | $FRI_{6-7}$ Beta (sig) | FRI Drop$_{6-7 to 8-9}$ Beta (sig) |
| --- | --- | --- | --- | --- | --- |
| $BE_{6-7\ cm}$ | .50 (<.007) | .28 (<.099) | −.53 (<.002) |  |  |
| BE drop$_{4-5 to 6-7\ cm}$ | .45 (<.018) | .10 <.526) | −.48 (<.005) |  |  |
| $BE_{8-9}$ | .69 (<.000) |  |  | .79 (<.000) | .46 (<.005) |
| BE drop$_{6-7 to 8-9}$ | .32 (<.19) |  |  | .04 (<.837) | .34 (<.097) |

38 cases had fetal scalp sample readings at both 4-5 cm and 6-7 cm. Just using the $FRI_{4-5\ cm}$ and the drop in FRI from In the foregoing FIGS. 7 and 8: "FRI5" represents FRI measured near the beginning of the period defined by the cervix's being dilated at 5 cm; "FRI10-5chg" represents the difference between the FRI at 10 cm dilatation and 5 cm dilatation; "PIOl" represents the predicted low BE, and the observed low BE; and "PhOh" represents the predicted high BE and the observed high BE; The "B's" from the equation represent the change in the natural logarithm of the odds of being in the low BE category change with a unit change in the independent variable. Here there are two independent variables, the initial FRI score at a certain dilatation and the extent of change in FRI between that dilatation and 10 cm's. Furthermore, "N's $R^2$" represents Nagelkerke's approximation of the $R^2$ derived from ordinary least squares regression; and "HL" is short for the Hosmer-Lemshaw coefficient. The more significant the Nagelkerke $R^2$ the better; the less significant the Hosmer-Lemeshow coefficient, the better (since it indicates that something important was not left out of the model).

The larger issue is the extent to which it is possible to predict the log odds of being in the bottom 30% of BE cases at the beginning of the 2nd stage of labor. The equations for cervical dilatations (CD) of 5-7 all have sufficiently large N's and are both consistent in their estimates and highly significant. The higher the initial FRI score and the less negative the trajectory, the less likely a fetus is to reach the bottom 30%. The potential utility of this approach as a screening tool for evaluating acidosis risk at the beginning of stage 2 is confirmed by ROC curve analysis of FIG. 9.

Surprisingly, consideration of the effects of Intrauterine Resuscitation (IR) into the model of FIG. 5 (by assessing the extent to which the use of IR has additive and/or interactive effects when paired with the base excess variables), either additively or as an interaction term coupled with BE1 or the drop in BE, adds nothing to the analysis; none of the additional coefficients are significant. Notably, this raises questions about IR in practice since the use of IR as a strategy for dealing with problematic oxygenation of the blood reaching the fetus is such an obvious choice for inclusion. Yet, looking at the correlation between BE1 and the use of IR (r=0.08) or the correlation between the drop in BE and IR use (r=−0.06), there is virtually no correlation, suggesting the decision to use IR by the attending physicians was not affected either by the level of BE1 or fluctuations in it across short periods of time.

Tables 7 and 8, below, show the results of further introducing into the acidemia risk model the Fetal Reserve Index (FRI) evaluation.

TABLE 7

Regression Results for Acidemia Risk Model Encompassing BE, FRI and IR

|  | B* | Sig | Exp(B) | Lower 95% CI for Exp(B)** | Upper 95% CI for Exp(B) |
|---|---|---|---|---|---|
| BE1 | −0.61 | 0.000 | 0.55 | 0.45 | 0.66 |
| BE_drop_1_2 | 0.60 | 0.000 | 1.81 | 1.23 | 2.68 |
| IRmerge | −0.11 | 0.810 | 0.90 | 0.36 | 2.21 |
| FRI1 | 0.21 | 0.840 | 1.24 | 0.16 | 9.85 |
| FRIdrop by IRmerge | −1.25 | 0.032 | 0.29 | 0.09 | 0.90 |
| Constant | −6.32 | 0.000 | 0.002 |  |  |

TABLE 8

Summary Classification Table and Test Characteristics for Model in Table 4

| Equation | Observed | |
|---|---|---|
| Predictions | <−12 BE | Normal BE |
| <−12 BE | 15 | 8 | 23 |
| Normal BE | 38 | 287 | 325 |
|  | 53 | 295 | 348 |

In the foregoing tables, "sensitivity" (true positives/(true positives+false negatives) is 17%; "specificity" (true negatives/(true negatives+false positives) is 97%; the Positive Likelihood Ratio (Sensitivity/1−Specificity) is 10.44; the "Negative Likelihood Ratio" (1−Sensitivity/Specificity) is 0.88; PPV (true positives/all cases tested as being positive) is 65%*; NPV (true negatives/all cases tested as negative) is 88%; and "Accuracy" (true positives and true negatives)/total is 87%.

These characteristics are quite good, net of the low Sensitivity. The total R square analog is not significantly different from the earlier model (R square=0.33), but the Homer-Lemeshow statistic (sig<0.63) suggests that not much is left out of the model.

Figure 9:
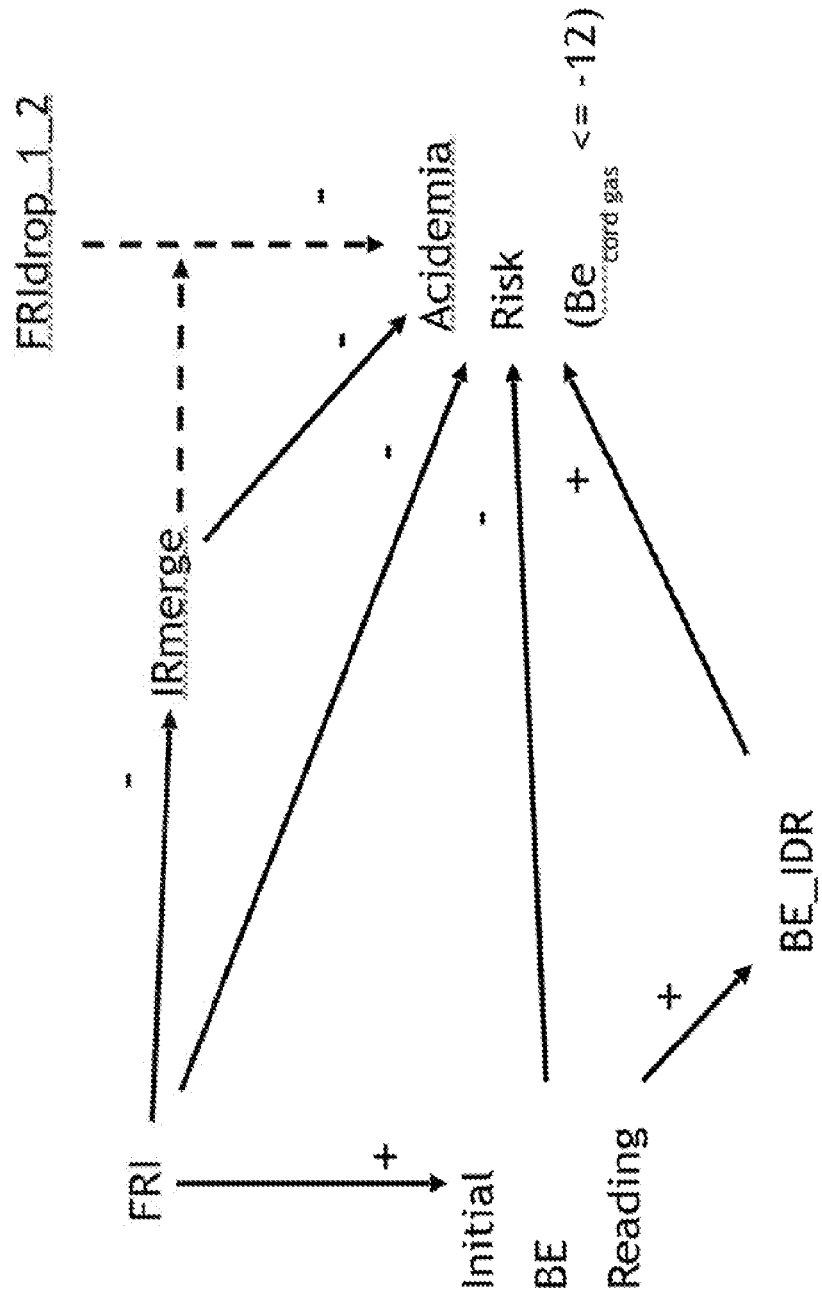
FIG. 9 is a diagrammatic depiction of a model showing the significance of the variables of initial BE value and the rate of drop thereof in relation to the risk of acidemia.

FIG. 9 represents a variant of the model of FIG. 5, additionally comprehending inclusion of FRI scores.

It is also possible to construct a model without the scalp-sampled BE readings—a procedure that has lapsed over the last few decades. Table 9 presents these results. While the amount of variance explained (R square ana-log=0.11) is about a third of that in the comprehensive model, the patterns are quite similar.

TABLE 9

Regression Results for a Acidemia Risk Model Encompassing FRI and IR

|  | B* | Sig | Exp(B) | Lower 95% CI for Exp(B)** | Upper 95% CI for Exp(B) |
|---|---|---|---|---|---|
| IRmerge | −0.47 | 0.28 | 0.62 | 0.26 | 1.47 |
| FRI | −2.12 | 0.017 | 0.11 | 0.02 | 0.67 |
| FRIdrop | 0.56 | 0.32 | 1.76 | 0.57 | 5.38 |
| FRIdrop by IRmerge | −2.17 | 0.006 | 0.11 | 0.02 | 0.54 |
| Constant | −0.47 | 0.37 | 0.63 |  |  |

Figure 10:
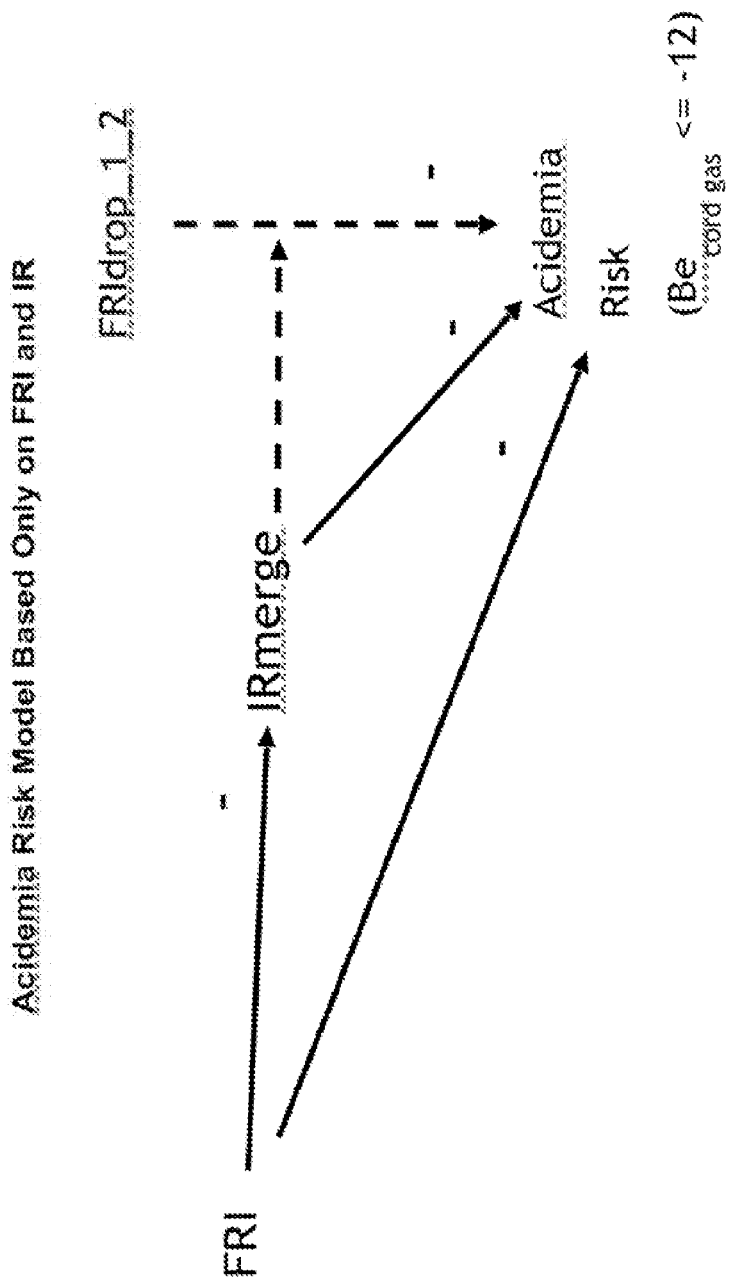
FIG. 10 is a diagrammatic depiction of a second model, showing the significance of the variables of initial FRI score, the rate of drop in FRI scores, initial BE value, and the rate of BE drop in relation to the risk of acidemia.

FIG. 10 represents a variant of the model of FIG. 9, excluding BE data.

IRmerge has both an additive and interactive effect (in conjunction with the drop in FRI) on the reduction of acidemia risk at birth, but the drop in FRI does not have a separate additive effect by itself. In terms of the characteristics of the model as a classification table (Table 10), sensitivity is very low at this point, but the PPV is considerably better.

TABLE 10

Classification Table and Test Characteristics for the Model In Table 6

| Equation | Observed | |
|---|---|---|
| Predictions | <−12 BE | Normal BE |
| <−12 BE | 2 | 2 | 4 |
| Normal BE | 52 | 293 | 345 |
|  | 54 | 295 | 349 |

In the foregoing, "Sensitivity" (true positives/(true positives+false negatives) is 4%; "Specificity" (true negatives/(true negatives+false positives) is 99%; the Positive Likelihood Ratio (Sensitivity/1−Specificity) is 5.46; the Negative Likelihood Ratio (1−Sensitivity/Specificity) is 0.97; the PPV (true positives/all cases tested as being positive) is 50%*; the NPV (true negatives/all cases tested as negative) is 85%; and Accuracy (true positives and true negatives)/total is 85%.

Figure 11:
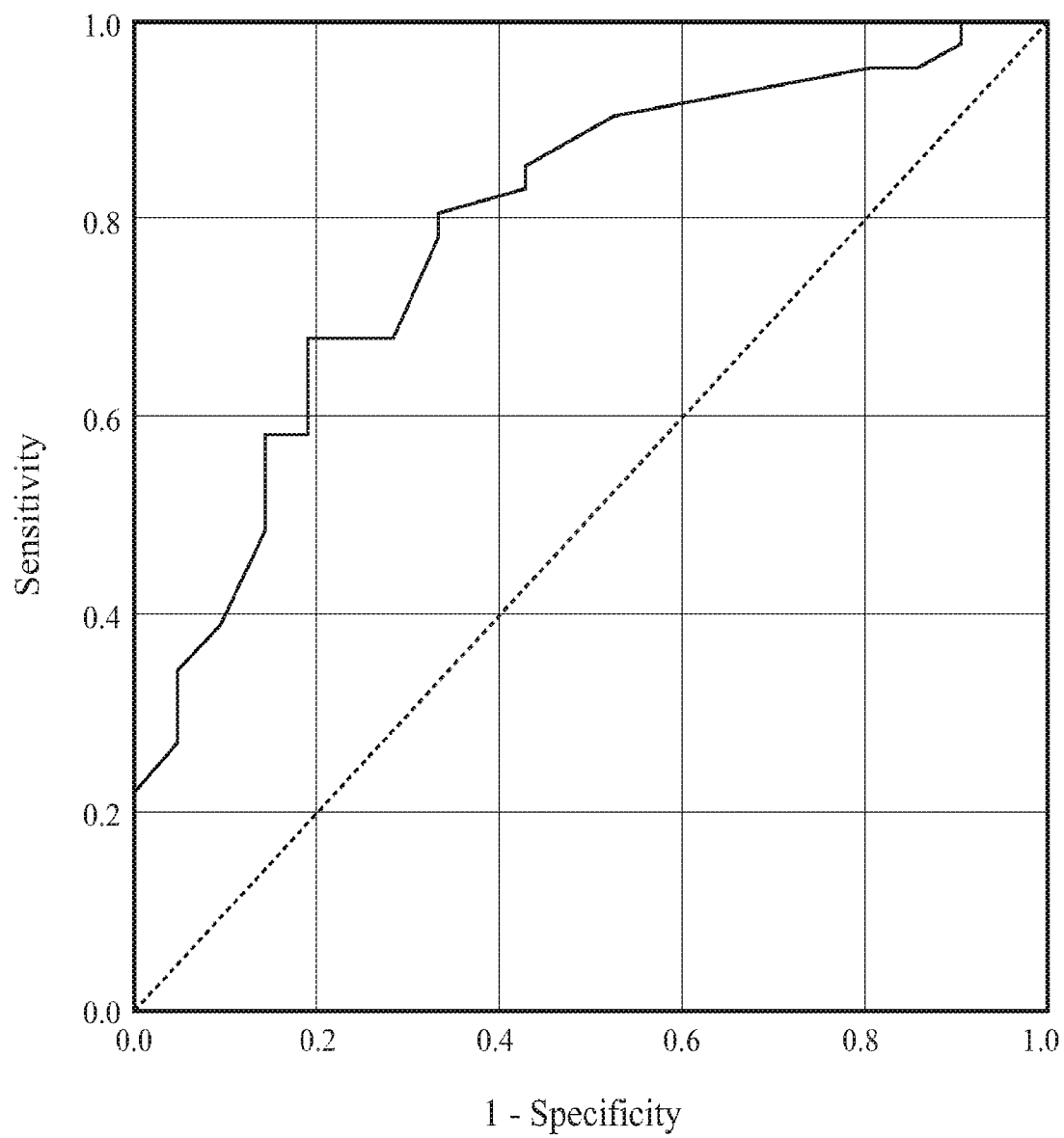
FIG. 11 depicts an ROC curve analysis of the BE initial drop rate (i.e., the rate of drop between first and second BE values). The straight line represents correspondence between sensitivity and specificity, i.e., ties.

Turning next to FIG. 11, there is shown an ROC curve depicting comparisons for acidemia (cord blood). Table 11, below, summarizes the area under the curve for the curve of FIG. 11.

TABLE 11

Area Under the Curve
Test Result Variable(s): Predicted probability

| Area | Std. Error[a] | Asymptotic Sig.[b] | Asymptotic 95% Confidence Interval | |
|---|---|---|---|---|
|  |  |  | Lower Bound | Upper Bound |
| 0.828 | 0.030 | 0.000 | 0.771 | 0.886 |

[a]Under the nonparametric assumption
[b]Null hypothesis: true area = 0.5

Figure 12:
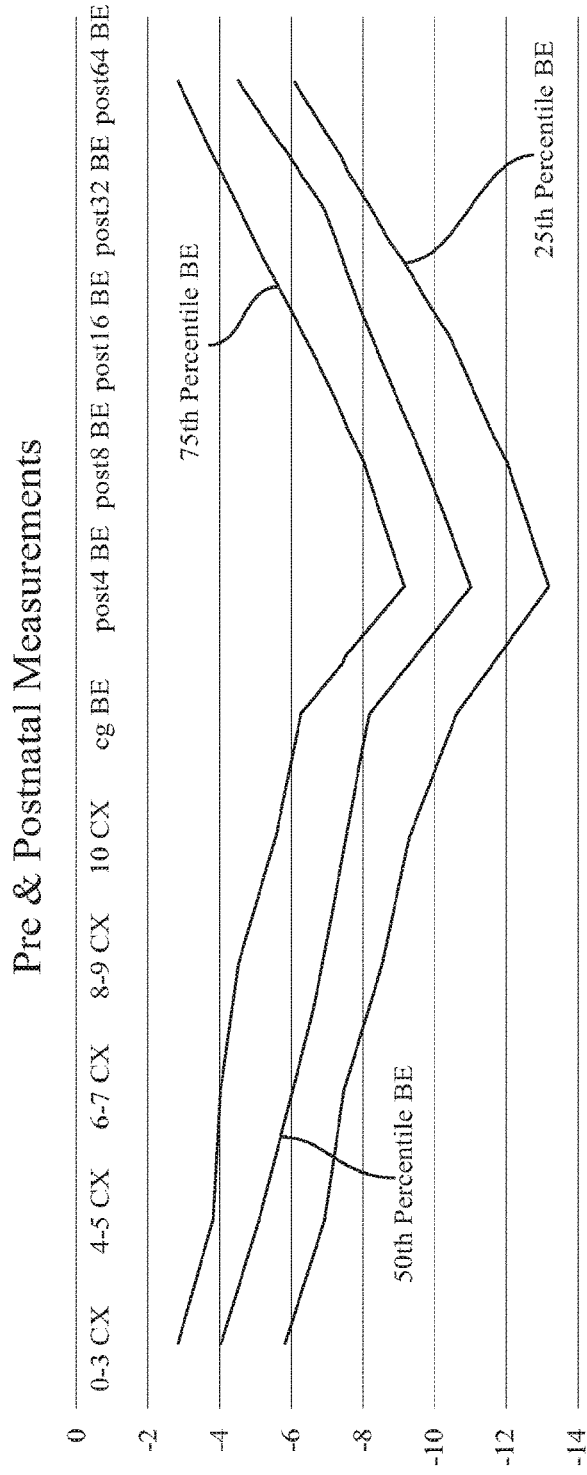
FIG. 12 graphs BE values against cervical dilatations and times post-partum for each of the $25^{th}$, $50^{th}$, and $75^{th}$ percentiles of BE value measurements.

Referring next to FIG. 12, the BE values are represented in three lines: the 75th (top line), 50th (middle line), and 25th (bottom line) percentile of BE measurements at the given dilatation, cord blood, and time postpartum, from early labor through the second stage, delivery, and 1 hour postpartum. The BE values create three parallel lines of change. Importantly, the IDR (not shown in the figure) can be used to predict very early on in labor the likelihood of the fetus/baby reaching a level of acidemia at high risk for damage and impairment. Moving up the assessment of risk for acidemia can lead to changes in obstetric care, e.g., earlier initiation of IR and possible transfer of the patient to a high-risk center early in labor, when such a transfer would be feasible.

Figure 13:
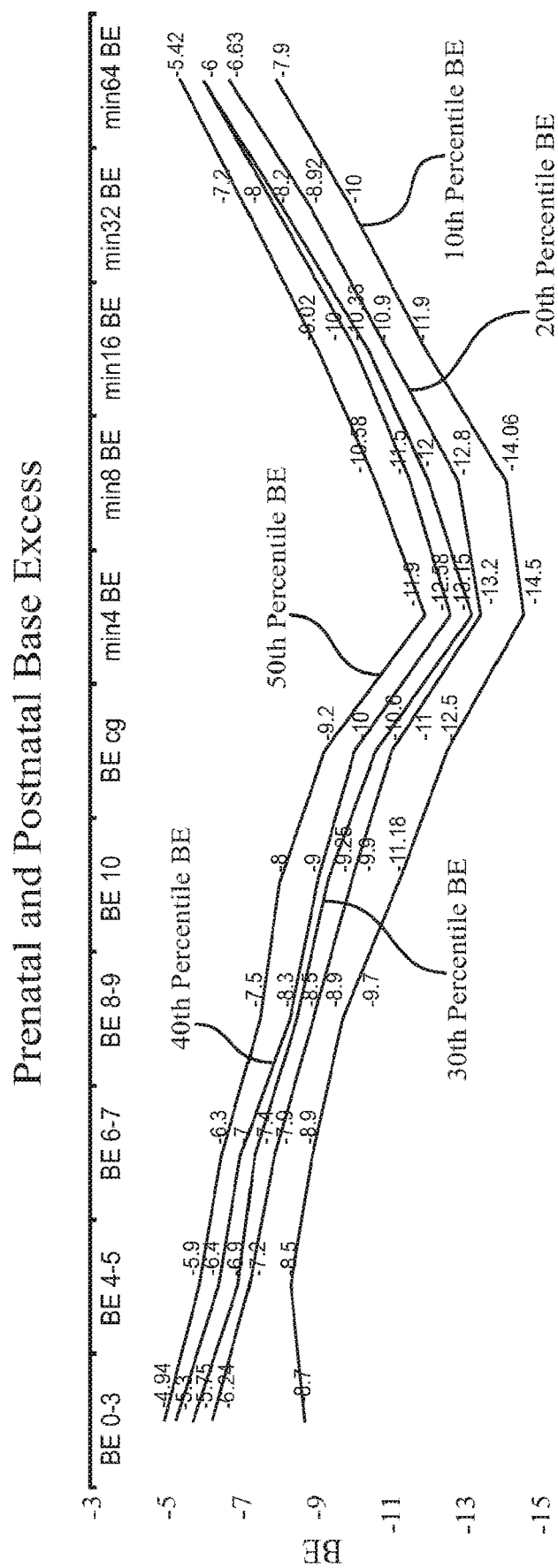
FIG. 13 graphs BE values against cervical dilatations and times post-partum for each of the $10^{th}$ (bottom line), $20^{th}$ (second line from bottom), $30^{th}$ (third line from bottom), $40^{th}$ (second line from top), and $50^{th}$ (top line) percentiles of BE value measurements.
Figure 14:
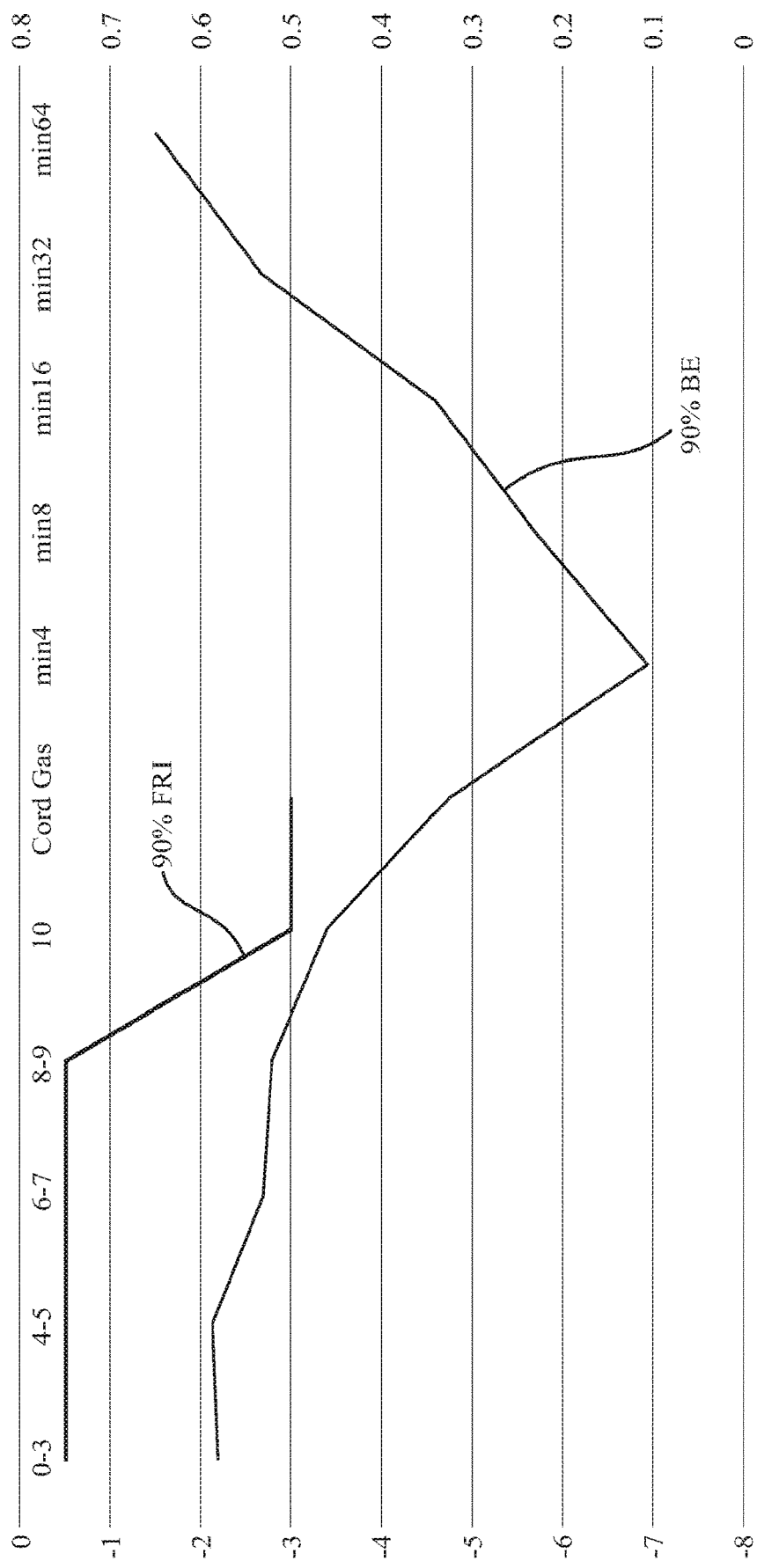
FIG. 14 graphs BE values against cervical dilatations and times post-partum, as well as FRI scores, for the $90^{th}$ percentile of BE value measurements.
Figure 15:
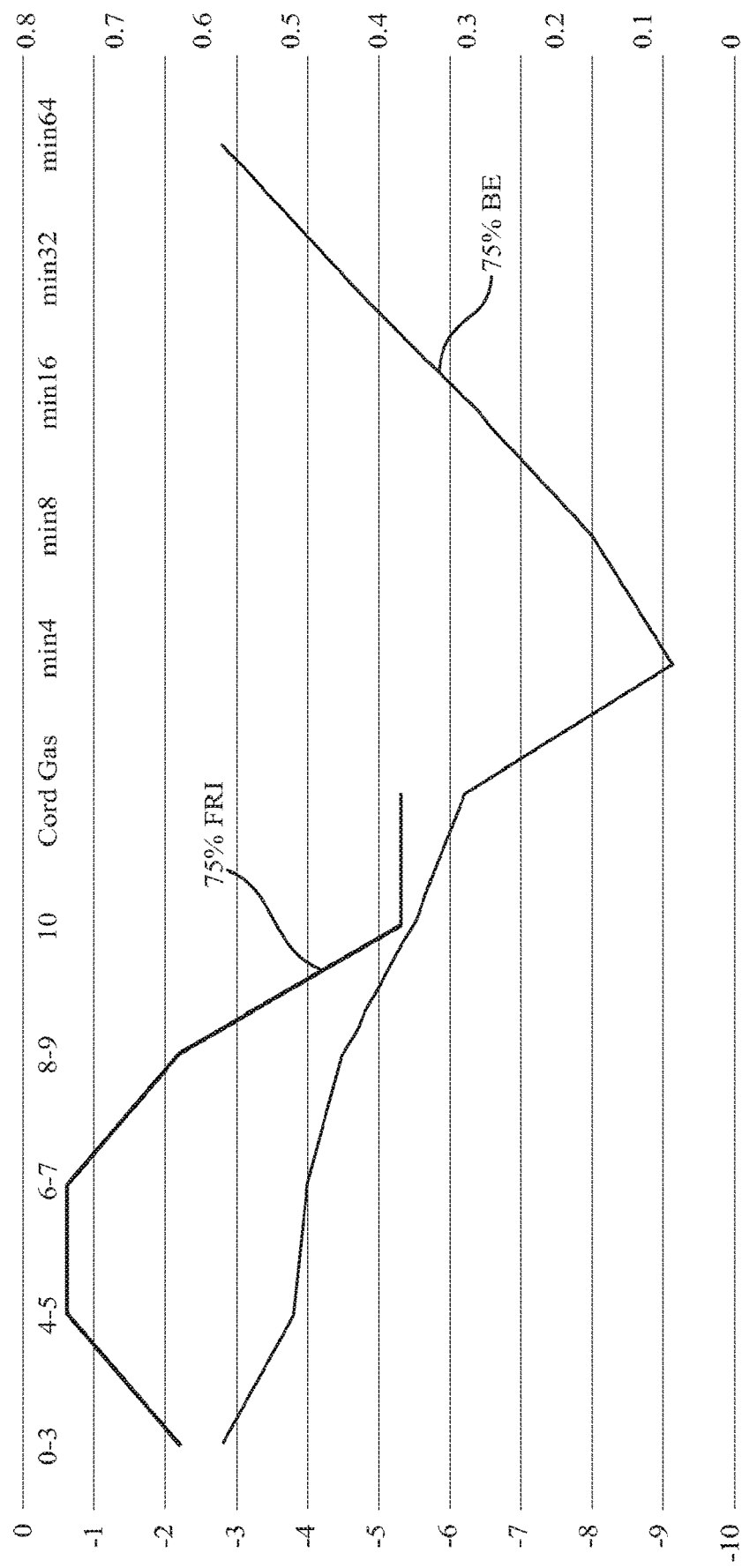
FIG. 15 graphs BE values against cervical dilatations and times post-partum, as well as FRI scores, for the $75^{th}$ percentile of BE value measurements.
Figure 16:
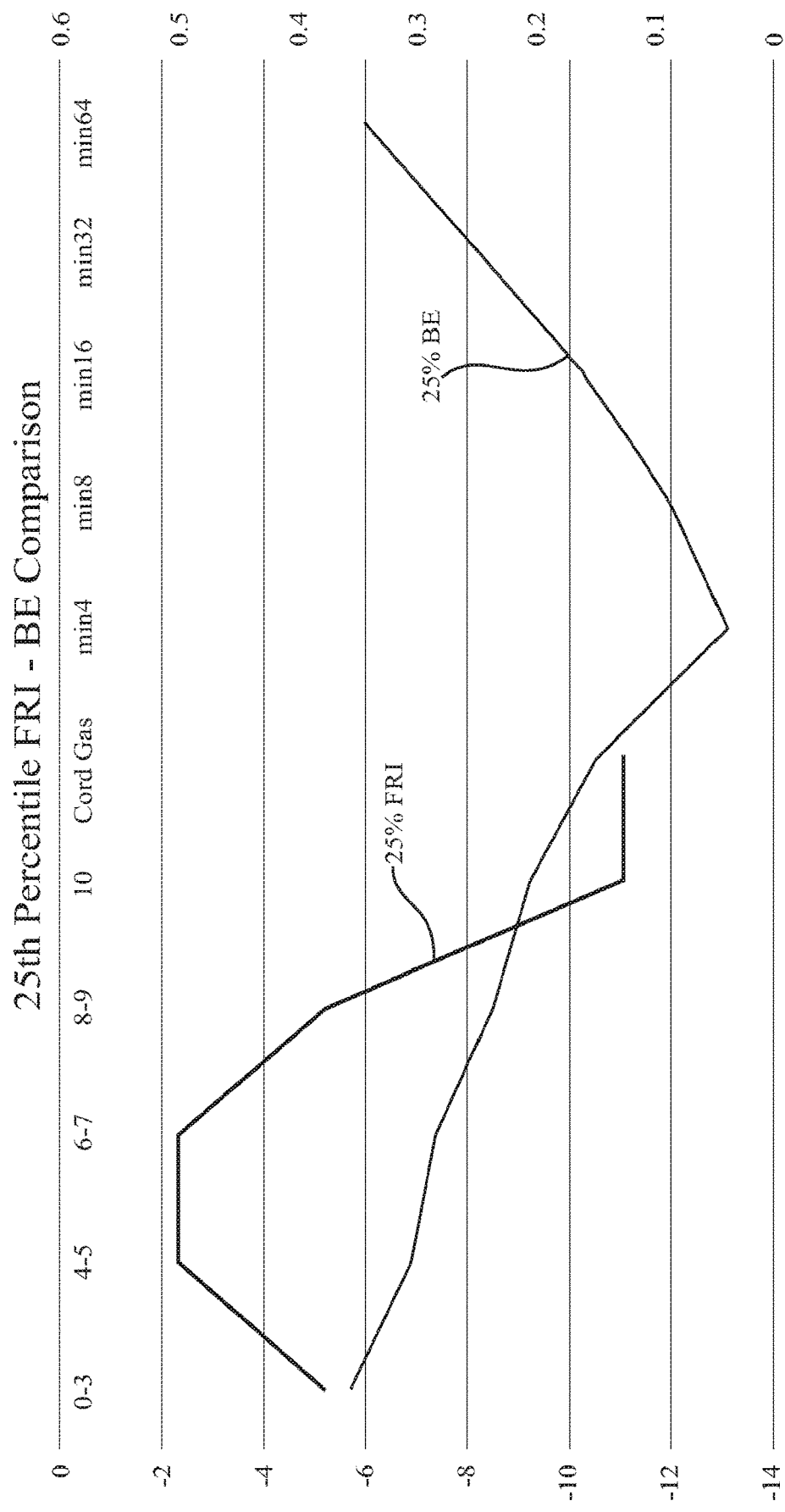
FIG. 16 graphs BE values against cervical dilatations and times post-partum, as well as FRI scores, for the $25^{th}$ percentile of BE value measurements.
Figure 17:
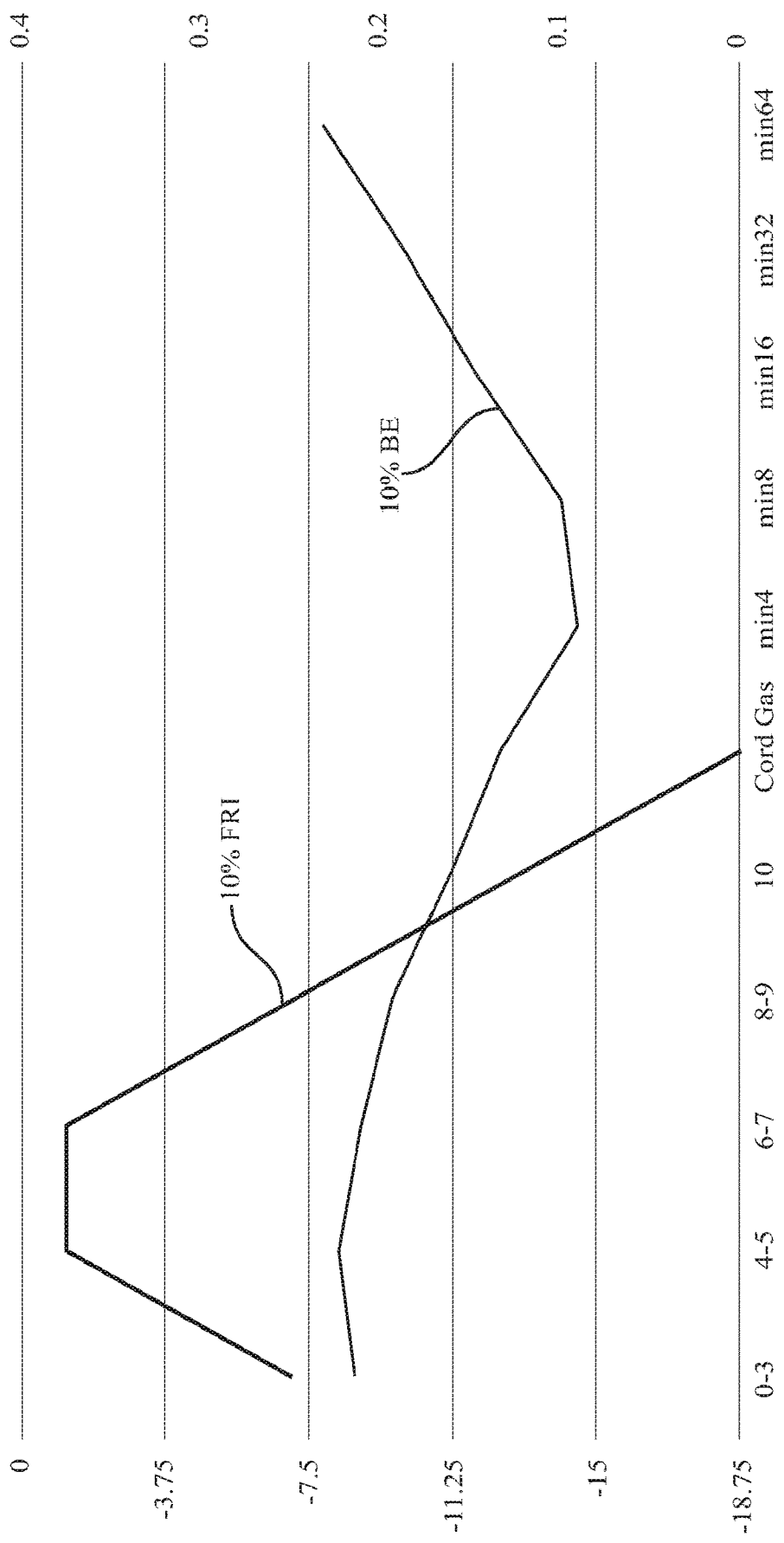
FIG. 17 graphs BE values against cervical dilatations and times post-partum, as well as FRI scores, for the $10^{th}$ percentile of BE value measurements.

Referring also to FIG. 13, further analysis of the lower portion of the curve shows that for the $10^{th}$ percentile (bottom line), the BE at birth (based on cord blood) is −12.5—already into the risk zone. It then precipitously drops over the next 4 minutes to −14.5 and stays in the danger zone until 16 minutes. This is the period of maximum risk of damage to the baby. By definition, 9% of cases actually do worse than this.

The data presented herein demonstrate that FRI, which is an indirect assessment of acidemia risk, correlates significantly with BE, making it useful to immediately suggest which patients should have fetal scalp, or other fetal blood, sampling to analyze BE. These data also suggest that both results (BE and FRI) can predict level of fetal risk and allow intervention earlier than currently possible.

In demonstration of the foregoing, FIGS. 14-17 depict three graphs showing the $90^{th}$, $75^{th}$, $25^{th}$, and $10^{th}$ percentiles of BE results (bottom lines in each graph), at the different cervical dilatations and time periods, plotted against the FRI results (top lines in each graph) for these same data. Again, these data show that the FRI score (top lines) can be used early on in labor as a screening test to decide on whom to perform a fetal scalp sample to get the BE value (bottom lines).

Figure 18:
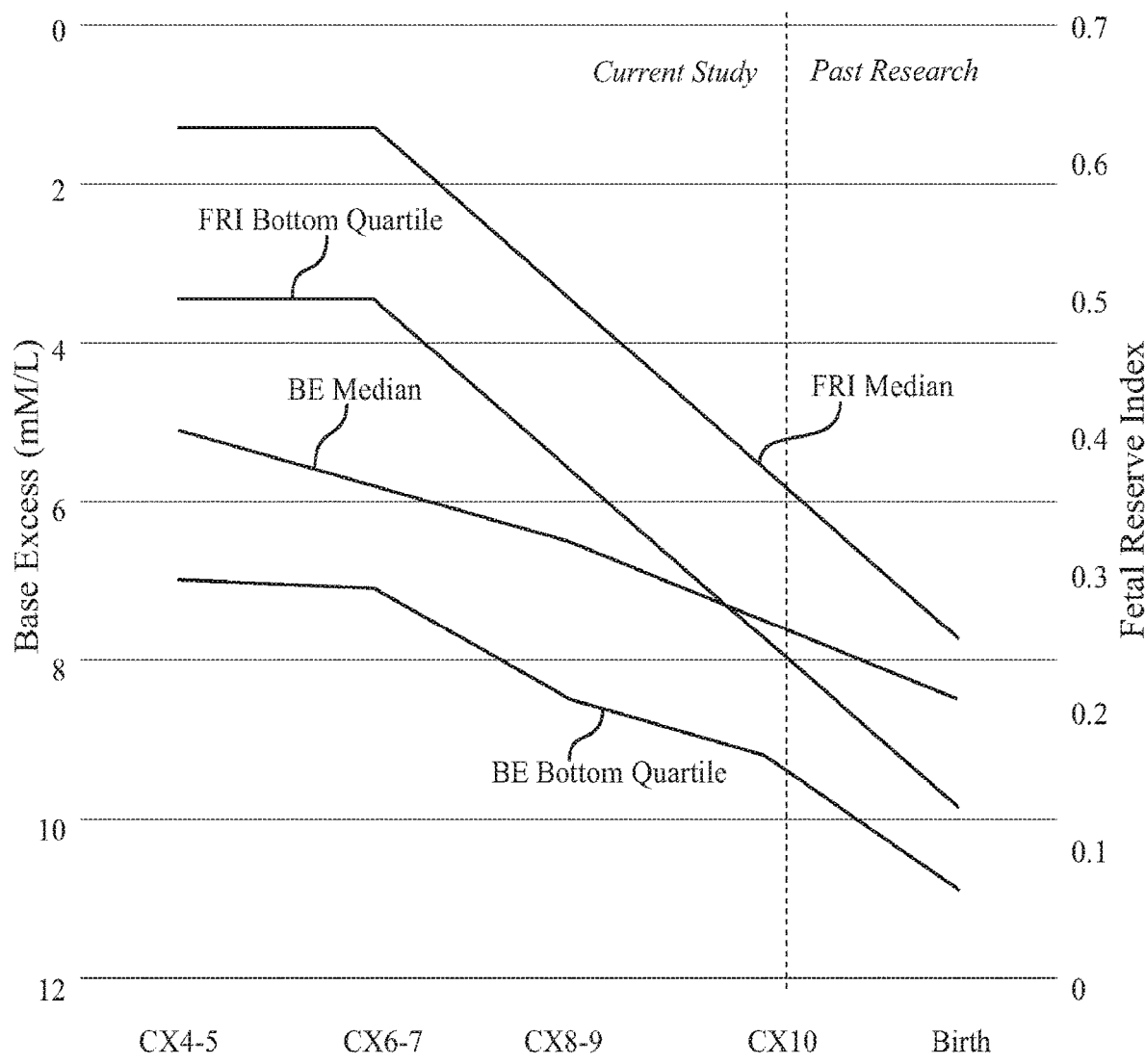
FIG. 18 graphs BE and FRI median and bottom-quartile values throughout the active stage of labor.

In further demonstration of the foregoing, FIG. 18 plots BE and FRI values at cervical dilatations of 4-5 (leftmost point on X axis), 6-7, 8-9, 10, and at birth (rightmost point on the X axis). The plots show measurements for the median BE values, BE values in the bottom quartile, median FRI scores, and FRI scores in the bottom quartile. Notably, the FRI scores are shown in FIG. 18 as fractional values between 0 and 1, with 1 representing a FRI score of 100.

Figure 19:
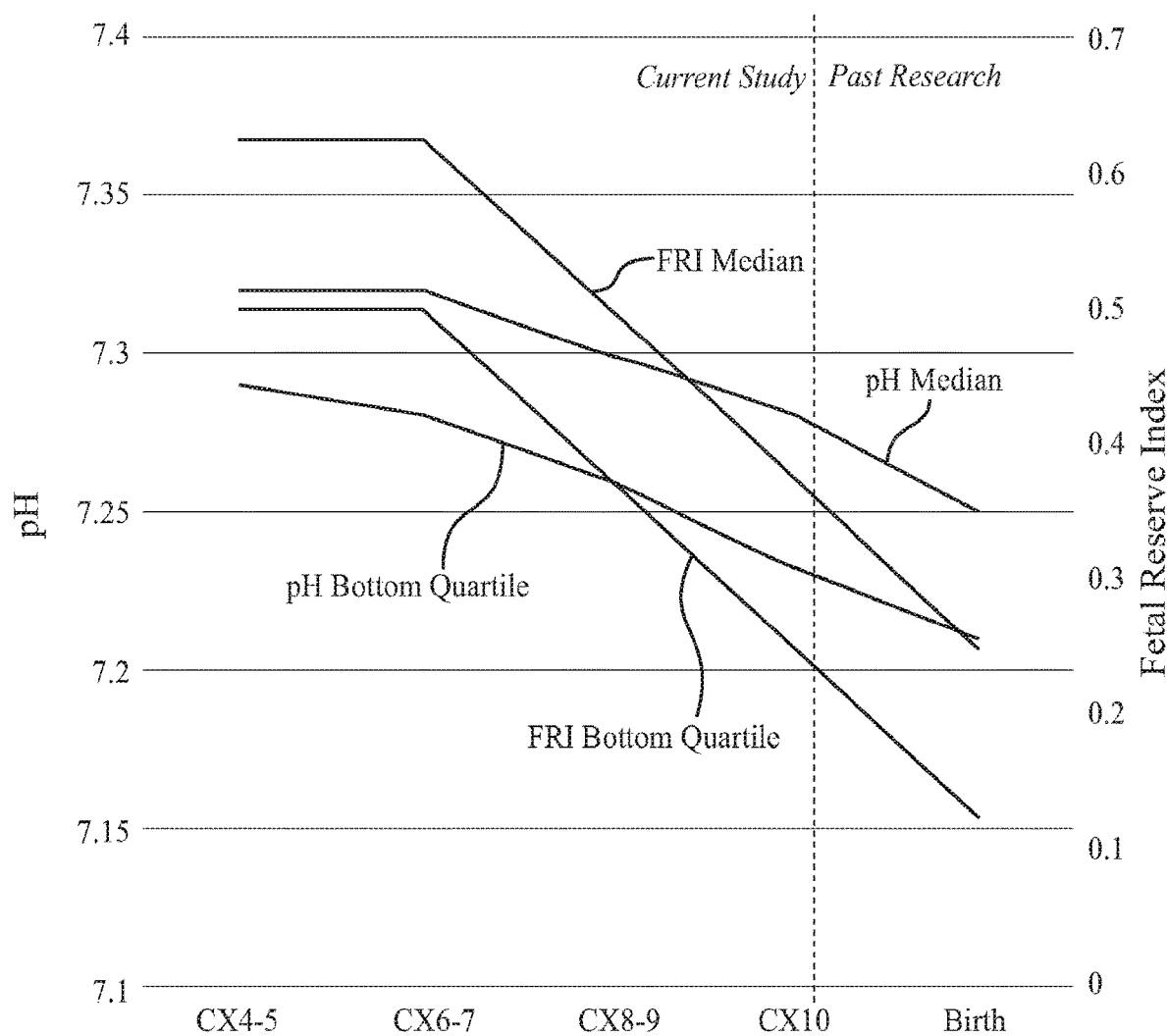
FIG. 19 graphs pH and FRI median and bottom-quartile values throughout the active stage of labor.

FIG. 19 similarly shows FRI scores plotted with pH measurements at cervical dilatations of 4-5 (leftmost point on X axis), 6-7, 8-9, 10, and at birth (rightmost point on the X axis). The plots show measurements for the median pH values, pH values in the bottom quartile, median FRI scores, and FRI scores in the bottom quartile. Notably, the FRI scores are shown in FIG. 19 as fractional values between 0 and 1, with 1 representing a FRI score of 100.

Figure 20:
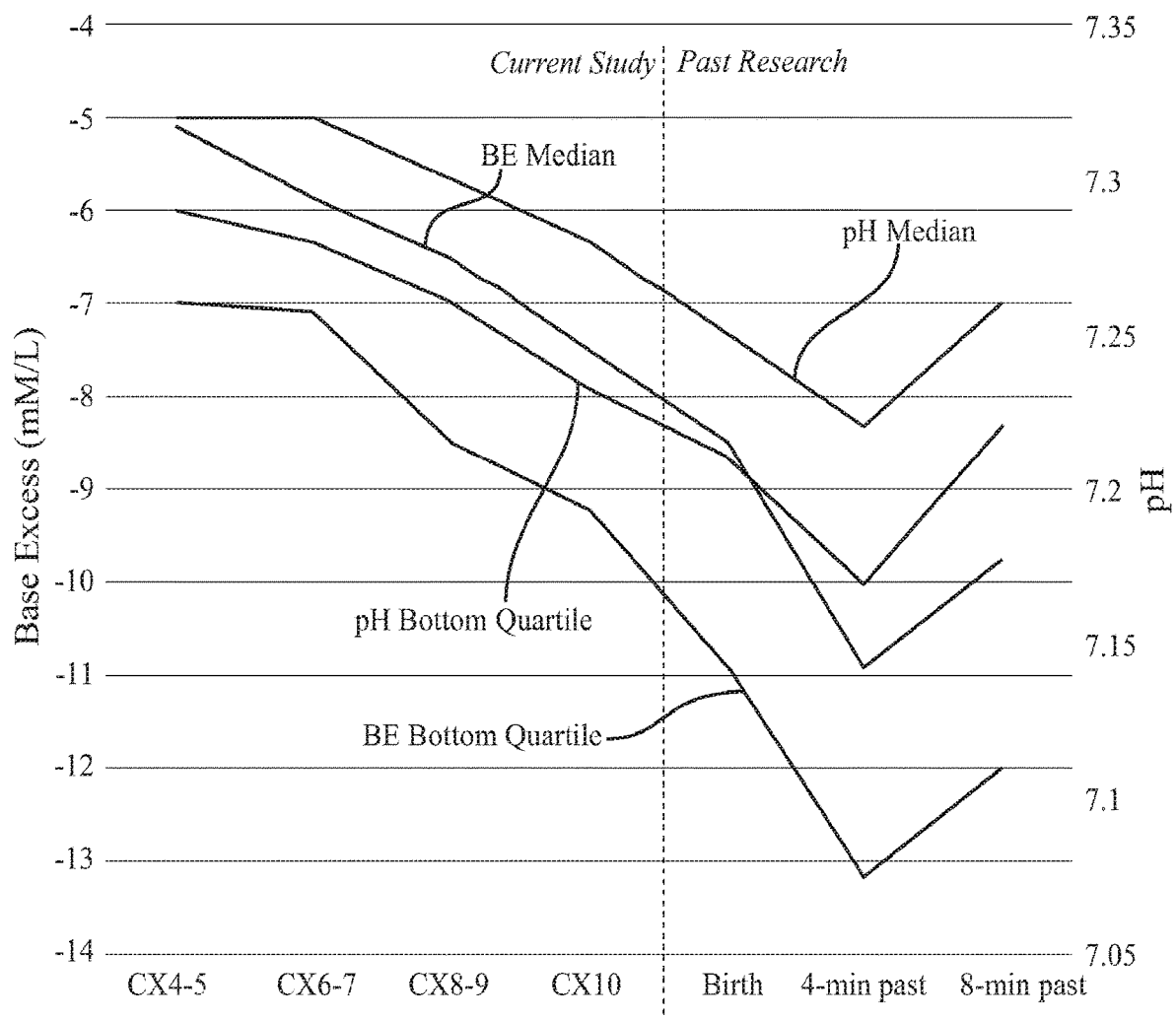
FIG. 20 graphs BE and pH median and bottom-quartile values throughout the active stage of labor.

Finally, FIG. 20 shows pH and BE measurements at cervical dilatations of 4-5 (leftmost point on X axis), 6-7, 8-9, 10, and at birth (rightmost point on the X axis). The plots show measurements for the median BE values, BE values in the bottom quartile, median pH scores, and pH scores in the bottom quartile.

Acidosis, as reflected by the BE value, has generally been the closest approximation to determining risk for impairment although experience to date has been insufficient to create precise estimates of risk for any given fetus. MoMs categorization makes immediate risk assessment easier to appreciate. Adding the trajectory improves the accuracy of risk level progression. Since it is very unlikely that continuous BE or pH measurements from early in labor will ever be routinely available, especially prior to the active phase of labor (<6 cms), the FRI and its trajectory appear to together be a reasonable surrogate for such. Combining the information available in FRI may permit an inference of the risk of acidosis at the beginning of the $2^{nd}$ stage and can also suggest when FSS might be considered. In sum, it is an improvement on CTG to predict acidosis and its sequelae.

The foregoing results support several methods for identifying, and reducing, the risk for neurological injury to the fetus.

A first such method comprehends conducting an analysis of fetal blood at a first period in time during labor, for example when cervical dilatation is from 0 to 3 cm, to determine at least a first base excess (BE) value for the fetus; then, determining a multiple of the median for the BE value at the first period in time by dividing the BE value by the median BE value of a dataset (e.g., such as employed in the analysis described herein) comprising a population of fetal BE values established at the same period in time during the first stage of labor as the first period. As discussed herein, a risk of neurological injury to the fetus is indicated when the BE value is a predefined multiple of the median (MoM) BE value (e.g., 1.5 at 0-3 cm dilatation). When risk to the fetus for neurological injury is indicated by the identification step, then treating the fetus by intervening in labor to reduce or eliminate the risk of neurological injury to the fetus through any conventional therapeutic measures.

Another method supported by this disclosure comprises identifying during labor the risk of neurological injury to a fetus by, (i) at a first period in time during the first stage of labor (e.g., when cervical dilatation is between 0-3 cm), conducting an analysis of fetal blood to determine at least a first BE value for the fetus. The risk of neurological injury to the fetus is indicated when the BE value is which value is determined from the analysis described above. Where the risk of neurological injury is indicated by the identification step, treatment is rendered by intervening in labor to reduce or eliminate the risk of neurological injury to the fetus through any conventional therapeutic measures—both in utero or deciding to deliver the baby expeditiously.

Another method supported by this disclosure comprises the following steps:
 (a) monitoring the fetus for at least a first set of concurrent clinical parameters indicative of a present level of risk for neurological injury to the fetus;
 (b) determining at a first period in time during the first stage of labor (e.g., when cervical dilatation is between 0-3 cm) a present level of risk to the fetus for neurological injury based on the first set of concurrent clinical parameters, wherein the determined present level of risk is expressed as the FRI value;
 (c) determining a MoM for the FRI value at the first period in time by dividing the FRI value by the median FRI value of a dataset (such as, for instance, the dataset described herein) comprising a population of FRI values established at the same period in time during the first stage of labor as the first period, wherein the risk for neurological injury is indicated when the MoM of the FRI value is a predefined multiple of the median FRI value; and
 (d) treating the fetus for which the risk of neurological injury is indicated by the step (c), wherein the treatment step comprises intervening in labor to reduce or eliminate the risk of neurological injury to the fetus through any conventional therapeutic measures.

When step (c) indicates the risk of neurological injury to the fetus, the data disclosed herein support the further step of conducting an analysis of fetal blood at at least a second period in time during the first stage of labor (e.g., when cervical dilatation is less than 10 cm) to determine at least a base excess (BE) value. As discussed, the BE value is a more accurate indicator of the risk of acidosis. Consequently, the FRI determination early on in labor facilitates discriminating between those babies in need of more invasive testing of fetal blood and those that are not.

The data disclosed herein also support the further step of conducting an analysis of fetal blood at a third period in time during the first stage of labor, the third period in time being later than the second point in time.

Another method supported by this disclosure utilizes the rate of drop in BE values determined during the course of the first stage of labor to identify and treat risk of neurological injury. This method comprises the steps of:

identifying during labor the risk of neurological injury to a fetus by: (i) at a first period in time during the first stage of labor (e.g., when cervical dilatation is from 0-3 cm), conducting an analysis of fetal blood to determine at least a first BE value for the fetus; (ii) at second period in time during the first stage of labor, later than the first point in time (e.g., after the first period but before cervical dilatation is at 10 cm), conducting an analysis of fetal blood to determine at least a second base excess (BE) value for the fetus; and (iii) determining a rate of drop from the first BE value to the at least second BE value, wherein a risk of neurological injury to the fetus is indicated when the rate of drop is at least a predetermined value—such as, by way of non-limiting example, 46% or greater. When the risk of neurological injury is indicated by the identification step, then intervention in labor to treat the fetus so as to reduce or eliminate the risk of neurological injury is undertaken.

Instead of comparing the BE rate of drop against a predefined percentage, the foregoing method may instead comprehend the step of determining a MoM for the rate of drop by dividing the rate of drop by the median rate of drop of a dataset (such as, for instance, described herein) comprising a population of rates of drop for fetal BE values established at the same periods in time during the first stage of labor as the first and second periods. According to this variant, a risk of neurological injury to the fetus is indicated when the MoM for the rate of drop is a predefined multiple of the median rate of drop. Intervention in labor to treat the fetus through any conventional therapeutic measures is then undertaken when the risk of neurological injury is indicated.

Another method supported by the data described herein comprises the steps of:
(a) monitoring the fetus for at least a first set of concurrent clinical parameters indicative of a present level of risk for neurological injury to the fetus;
(b) determining at a first period in time during or before labor a present level of risk to the fetus for neurological injury based on the first set of concurrent clinical parameters, wherein the determined present level of risk is expressed as a numerical value (FRI value);
(c) determining at a second period in time during or before labor, later than the first period in time, a present level of risk to the fetus for neurological injury based on the first set of concurrent clinical parameters, wherein the determined present level of risk is expressed as a FRI value;
(d) determining a rate of drop from the first FRI value to the second FRI value;
(e) determining a multiple of the median (MoM) for the FRI value at the first period in time by dividing the FRI value by the median FRI value of a dataset comprising a population of FRI values established at the same period in time during or before the first stage of labor as the first period, wherein the risk for neurological injury is indicated when the MoM of the FRI value is a predefined multiple of the median FRI value; and
(f) determining a MoM for the rate of drop by dividing the rate of drop by the median rate of drop of a dataset comprising a population of rates of drop for FRI values established at the same periods in time during or before the first stage of labor as the first and second periods, wherein the existence of neurological injury to the fetus is indicated when the MoM for the rate of drop is a predefined MoM rate of drop.

Another method for reducing the risk of neurological injury to a human fetus during labor that is supported by the data described herein comprises the steps of:
(a) monitoring the fetus for at least a first set of concurrent clinical parameters indicative of a present level of risk for neurological injury to the fetus;
(b) determining at a first period in time during or before labor (e.g., a cervical dilatation of between 0-3 cm) a present level of risk to the fetus for neurological injury based on the first set of concurrent clinical parameters, wherein the determined present level of risk is expressed as a numerical value (FRI value);
(c) determining at a second period in time during or before labor (e.g., a cervical dilatation of less than or equal to 10 cm), later than the first period in time, a present level of risk to the fetus for neurological injury based on the first set of concurrent clinical parameters, wherein the determined present level of risk is expressed as a FRI value;
(d) determining a rate of drop from the first FRI value to the second FRI value, wherein a risk of neurological injury to the fetus is indicated when the rate of drop is greater than a predefined value (for instance, but without limitation, a rate of drop of 46% or greater); and
treating the fetus for which the risk of neurological injury is indicated by the identification step, wherein the treatment step comprises intervening in labor to reduce or eliminate the risk of neurological injury to the fetus through any conventional therapeutic measures.

The MoMs approach described herein can be considered as an increased "magnification" of the metabolic risk assessment. It is possible, by the methods disclosed herein, to immediately understand the risk of a measurement without having to immediately seek to contextualize it with the progress of labor. Moreover, focusing on early data collection in labor, pursuant to the present invention, helps to clarify those fetuses who have come in to labor "clean" and for whom worsening status in labor by FRI and MoMs can prevent damage from those who were likely already damaged at the time of admission.

A significant medico-legal issue in obstetrics is trying to determine if a baby was damaged in labor or came into labor already damaged. Because interpretation of EFM has been so subjective, there is no widespread consensus and, thus, no reliable guidance for practitioners to follow in making this determination. In medico-legal situations, such often leads to diametrically opposed opinions being presented by medical experts. It will be appreciated that the admissions and maintenance assessment methodologies discussed herein provide objective guidance for making these determinations.

The data presented here suggest that combination of assessing BE early in labor, as well as how fast it subsequently drops, provides a sensitive method for the early prediction of risk of metabolic acidosis. It does so before there are any abnormalities of EFM. Furthermore, these data show that the initial FRI and FRI initial drop rate provide a useful screen to decide on whom to perform fetal scalp sampling or other fetal blood analysis to then determine the level of acidosis risk at birth. Such earlier identification of risk might allow earlier initiation of intrauterine resuscitation, which has previously been shown to reduce likelihood and duration of metabolic acidosis, risk for neurologic compromise, and the need for emergency deliveries.

Embodiments of the foregoing methods are envisioned which utilize specialized equipment or general purpose computers, tablet computers, smartphones, etc. to receive various sensor inputs (manually and/or automatically received), perform various determining steps of the methods described herein, and provide visual and/or audio indications of risk and/or recommendations for intervention.

It is contemplated that the above-specified methodologies may be implemented by, for instance, apparatus comprising at least one computer.

In one embodiment, such an apparatus comprises at least one computer operative to determine, for a first base excess (BE) value for the fetus established at a first period in time during the first stage of labor, a multiple of the median for the BE value at the first period in time by dividing the BE value by the median BE value of a dataset comprising a population of fetal BE values established at the same period in time during the first stage of labor as the first period. The at least one computer is further operative to indicate a risk of neurological injury to the fetus when the BE value is a predefined multiple of the median BE value.

It will be appreciated by those skilled in the art that the at least one computer, or even another computer operatively connected to the at least one computer, may be programmed with the dataset comprising a population of fetal BE values established at the same period in time during the first stage of labor as the first period.

In another embodiment, the apparatus comprises at least one computer operative to: receive input signals indicative of at least a first set of concurrent clinical parameters indicative of a present level of risk for neurological injury to the fetus; determine at a first period in time during or before labor a present level of risk to the fetus for neurological injury based on the first set of concurrent clinical parameters, wherein the determined present level of risk is expressed as a numerical value (the first FRI value); determine a multiple of the median (MoM) for the first FRI value by dividing the first FRI value by the median FRI value of a dataset comprising a population of FRI values established at the same period in time during or before the first stage of labor as the first period; and provide an output (i) indicating a risk for neurological injury when the determined MoM of the first FRI value is a predefined multiple of the median FRI value, and/or (ii) indicating the existence of neurological injury to the fetus when the MoM for the rate of drop is a predefined MoM rate of drop.

Again, it will be appreciated by those skilled in the art that the at least one computer, or even another computer operatively connected to the at least one computer, may be programmed with the dataset comprising a population of FRI values established at the same period in time during or before the first stage of labor as the first period.

Still further, the at least one computer of this embodiment may be operative to: receive inputs indicating base excess (BE) values for the fetus at at least second and third periods in time during the first stage of labor, wherein the third period in time is later than the second point in time; determine a rate of drop for the BE values at the second and third periods in time; and provide an output indicating a risk for neurological injury when the BE values at the second and third periods in time reflect a rate of drop greater than a predefined value—for instance, 46%.

In another embodiment, the apparatus comprises at least one computer operative to receive inputs indicating base excess (BE) values for the fetus at at least first and second periods in time during the first stage of labor, wherein the second period in time is later than the first point in time, to determine a rate of drop for the BE values at the first and second periods in time, and provide an output indicating a risk for neurological injury when the BE values at the second and third periods in time reflect a rate of drop greater than a predefined value—for instance, 46%.

In another embodiment, the apparatus comprises at least one computer operative to: receive inputs indicating base excess (BE) values for the fetus at at least first and second periods in time during the first stage of labor, wherein the second period in time is later than the first point in time; determine a rate of drop from for the first BE value to the second BE value; determine a multiple of the median (MoM) for the rate of drop by dividing the rate of drop by the median rate of drop of a dataset comprising a population of rates of drop for fetal BE values established at the same periods in time during the first stage of labor as the first and second periods; and provide an output indicating a risk for neurological injury when the MoM for the rate of drop is a predefined multiple of the median rate of drop.

In another embodiment, the apparatus comprises at least one computer operative to receive input signals indicative of at least a first set of concurrent clinical parameters indicative of a present level of risk for neurological injury to the fetus; to determine at a first period in time during or before labor a present level of risk to the fetus for neurological injury based on the first set of concurrent clinical parameters, wherein the determined present level of risk is expressed as a numerical value (the first FRI value); to determine at a second period in time during or before labor, later than the first period in time, a present level of risk to the fetus for neurological injury based on the first set of concurrent clinical parameters, wherein the determined present level of risk is expressed as a second FRI value; to determine a rate of drop from the first FRI value to the second FRI value; and to provide an output indicating a risk for neurological injury when the determined rate of drop from the first FRI value to the second FRI value is at least a predetermined rate of drop.

In another embodiment, the apparatus comprises at least one computer operative to:
  receive input signals indicative of at least a first set of concurrent clinical parameters indicative of a present level of risk for neurological injury to the fetus;
  determine at a first period in time during or before labor a present level of risk to the fetus for neurological injury based on the first set of concurrent clinical parameters, wherein the determined present level of risk is expressed as a numerical value (the first FRI value);
  determine at a second period in time during or before labor, later than the first period in time, a present level of risk to the fetus for neurological injury based on the first set of concurrent clinical parameters, wherein the determined present level of risk is expressed as a second FRI value;
  determine a rate of drop from the first FRI value to the second FRI value;
  determine a multiple of the median (MoM) for the first FRI value by dividing the first FRI value by the median FRI value of a dataset comprising a population of FRI values established at the same period in time during or before the first stage of labor as the first period;

determine a MoM for the rate of drop by dividing the rate of drop by the median rate of drop of a dataset comprising a population of rates of drop for FRI values established at the same periods in time during or before the first stage of labor as the first and second periods; and provide an output (i) indicating a risk for neurological injury when the determined MoM of the first FRI value is a predefined multiple of the median FRI value, and/or (ii) indicating the existence of neurological injury to the fetus when the MoM for the rate of drop is a predefined MoM rate of drop.

In an exemplary form, the first period in time during labor is characterized by a cervical dilatation of between 0-3 cm; and the second period in time during labor is characterized by a cervical dilatation of less than or equal to 10 cm.

In one example, the risk of neurological injury to the fetus is indicated when the rate of drop is 46% or greater.

As discussed elsewhere, the first set of concurrent clinical parameters in the foregoing may comprise (a) FHR, (b) baseline FHR variability, (c) FHR accelerations, (d) FHR decelerations, and (e) maternal uterine contractions. Where such parameters are employed, the at least one computer is further operative to determine at the first period in time whether each concurrent clinical parameter (a) through (e) independently exhibits at least one non-reassuring characteristic, and to transform the number of the concurrent clinical parameters (a) through (e) that simultaneously, independently exhibit at least one non-reassuring characteristic into the first FRI value. This may be accomplished, for instance, by the implementation of a simple algorithm which adds the number of said parameters (a) through (e) that are simultaneously, independently non-reassuring, using arbitrarily assigned values (e.g., 1 or 0) for each.

The output of the foregoing embodiments may take any conventional form, including one or more of a graphical display, warning lights and/or sounds, etc, These outputs may be provided via the apparatus itself. They may also, or alternatively, be provided via peripheral apparatus, such as a video display and/or a printer.

It is also contemplated that the apparatus comprehended by this disclosure may, alternatively or in addition, be operative to provide other information, including FHR tracings, uterine activity tracings, and/or further information related to the level of risk presently indicated for the fetus, including, by way of non-limiting example, instructions to the clinician or clinicians pertaining to a predetermined action required or recommended for the identified level of risk. Such other information may be provided through the at least one output, for example.

The at least one computer is further operative to receive (such as via conventional means, like a keyboard, or mouse in combination with a graphical user-interface, for example), user-inputs indicative of BE values taken in accordance with the methodologies described above.

It is contemplated that apparatus according to the present invention may comprise a self-contained unit comprising the one or more sensors capable of monitoring/receiving user-inputs indicative of the aforementioned parameters, or a separate unit which receives inputs corresponding to these parameters from other, separate sensors. If the former, the at least one output may, as noted, further be able to provide outputs including one or more of a display and/or printout showing FHR and maternal uterine contraction tracings, such as would be provided with conventional FHM and uterine contraction sensors. If the latter, the apparatus for implementing the inventive methodologies may be separate apparatus connectable to a FHM device and capable of receiving data therefrom.

According to another embodiment of the inventive apparatus, the identification of the level of fetal risk can be provided remotely, such as via the internet or other computer network. According to this embodiment, it is contemplated that one or more persons, such as, for instance, one or more doctors and/or nurses in a geographically remote location, are provided a display/interface operatively connected to the apparatus at the site where the patient is located, such that the one or more remotely situated persons are presented with the identification of the level of risk to the fetus and, as desired, FHM and/or other parameters monitored so as to be capable of assisting (including via the interface and/or via other means such as a telephone, video-conference apparatus, etc.) those in the delivery room with the childbirth. For example, this system could be implemented in community hospitals lacking sufficient obstetricians in the delivery room.

In an exemplary implementation, the foregoing or other apparatus operable to perform the inventive method is operatively connected to a patient (either directly or via other monitoring apparatus) to monitor FHR. Continuously or periodically according to a desired schedule, baseline FHR variability, FHR accelerations, and FHR decelerations are determined from the FHR, and the parameters (a) through (d) are compared against known characteristics of non-reassurance, such as those specified herein, stored in the at least one computer, to determine whether any one or more parameters independently exhibits at least one non-reassuring characteristic. When the at least one computer determines that any non-reassuring characteristics are simultaneously present for any one or more parameters (a) through (d), that determination results in an indication of the corresponding level of risk to the fetus via one or more outputs. Furthermore, the apparatus will preferably provide an indication of the action required by/recommended for the clinician or other user.

Figure 21:
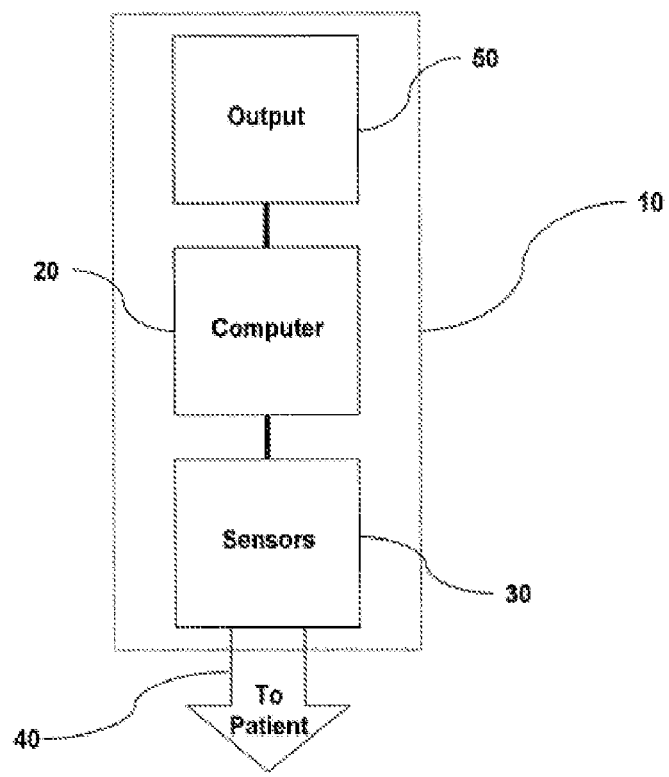
FIG. 21 is a diagrammatic depiction of an exemplary construction for an apparatus for implementing the inventive method.
Figure 22:
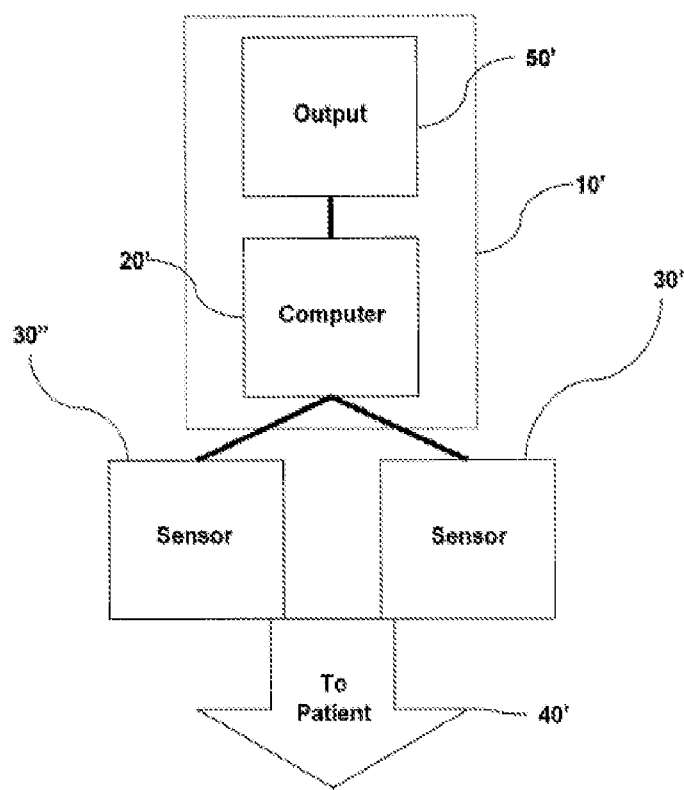
FIG. 22 is a diagrammatic depiction of a second exemplary construction for an apparatus for implementing the inventive method.
Figure 23:
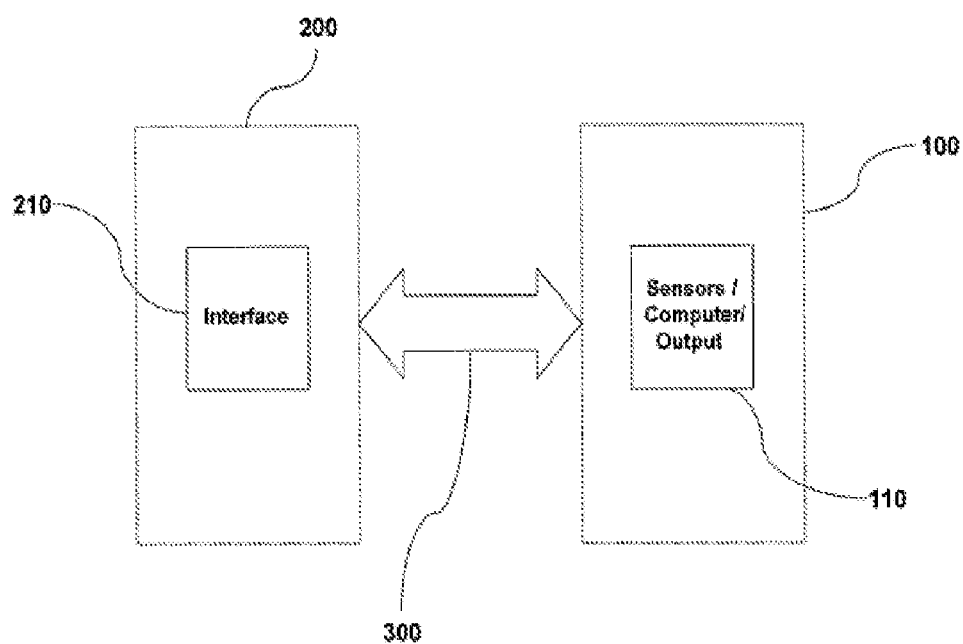
FIG. 23 is a diagrammatic depiction of an embodiment of an apparatus for implementing the inventive method providing for remote monitoring and/or feedback.

FIGS. 21 through 23 schematically depict exemplary, but by no means limiting, apparatus for carrying out the methods described above.

More particularly, FIG. 21 shows an apparatus 10 comprising at least one computer 20 operative to receive input signals, such as from one or more sensors 30 connected to a patient 40. At least one output 50 is operatively connected to the at least one computer 10. Operative connection of these various elements 20, 30 and 50, which may be accomplished by any known means, is indicated by bold lines in FIG. 21. The at least one output 50 may comprise, for example, a video display and/or a printer, warning lights (such as, for instance, a plurality of score-specific lights each corresponding to a different level of risk), an audible alarm, etc. It is also contemplated that the apparatus may, alternatively or in addition, be operative to provide other information, including FHR tracings, uterine activity tracings, and/or further information related to the level of risk presently indicated for the fetus, including, by way of non-limiting example, instructions to the clinician or clinicians pertaining to a predetermined action required or recommended for the identified level of risk. Such other information may be provided through the at least one output 50, for example. The at least one computer 20 is further operative to receive user-inputs (such as via conventional means, like a keyboard, or mouse in combination with a graphical user-interface, for example). It is contemplated that the apparatus 10 may comprise a self-contained unit comprising the one or more sensors 30 capable of monitoring/receiving user-inputs indicative of the aforementioned parameters, such as shown diagrammatically in FIG. 22, or a separate unit 10' which receives inputs corresponding to these parameters from other, separate sensors 30', 30" (FIG. X).

According to another embodiment (FIG. 23), the identification of the level of fetal risk can be provided remotely, such as via the internet or other computer network (indicated at 300). According to this embodiment, it is contemplated that one or more persons, such as, for instance, one or more doctors and/or nurses in a geographically remote location 200, are provided a display/interface 210 operatively connected to the apparatus 110 at the site where the patient is located 100, such that the one or more remotely situated persons are presented with the identification of the level of risk to the fetus so as to be capable of assisting (including via the interface and/or via other means such as a telephone, video-conference apparatus, etc.) those in the delivery room with the childbirth. For example, this system could be implemented in community hospitals lacking sufficient obstetricians in the delivery room. The foregoing description of the exemplary embodiments of the invention has been presented for purposes of illustration and description. It is not intended to be exhaustive or to limit the invention to the precise forms disclosed, and modifications and variations are possible in light of the above teachings or may be acquired from practice of the innovation. The embodiments are shown and described in order to explain the principles of the innovation and its practical application to enable one skilled in the art to utilize the innovation in various embodiments and with various modifications as are suited to the particular use contemplated. Although only a few embodiments of the present innovations have been described in detail in this disclosure, those skilled in the art who review this disclosure will readily appreciate that many modifications are possible without materially departing from the novel teachings and advantages of the subject matter recited. Accordingly, all such modifications are intended to be included within the scope of the present innovations. Other substitutions, modifications, changes and omissions may be made in the design, operating conditions and arrangement of the exemplary embodiments without departing from the spirit of the present innovations.

The invention in which an exclusive property or privilege is claimed is defined as follows:

1. A method for reducing the risk of neurological injury to a human fetus before or during labor, comprising the steps of:
    (a) monitoring the fetus for at least a first set of concurrent clinical parameters indicative of a present level of risk for neurological injury to the fetus;
    (b) determining at a first period in time before or during the first stage of labor a present level of risk to the fetus for neurological injury based on the first set of concurrent clinical parameters, wherein the determined present level of risk is expressed as a numerical value (the first FRI value);
    (c) determining a multiple of the median (MoM) for the FRI value at the first period in time by dividing the FRI value by the median FRI value of a dataset comprising a population of FRI values established at the same period in time during or before the first stage of labor as the first period, wherein the risk for neurological injury is indicated when the MoM of the FRI value is a predefined multiple of the median FRI value; and
    (d) treating the fetus for which the risk of neurological injury is indicated by the step (c), wherein the treatment step comprises intervening before or during labor to reduce or eliminate the risk of neurological injury to the fetus through any conventional therapeutic measures.

2. The method of claim 1, wherein, when the risk of neurological injury is indicated by the step (c), the method comprises the further step of conducting an analysis of fetal blood at at least second and third periods in time during the first stage of labor, the third period in time being later than the second point in time, and determining at least a base excess (BE) value for each of the second and third periods in time.

3. The method of claim 2, wherein the second and third periods in time during labor are each characterized by a cervical dilatation of less than 10 cm.

4. The method of claim 1, wherein the first set of concurrent clinical parameters comprise (a) FHR, (b) baseline FHR variability, (c) FHR accelerations, (d) FHR decelerations, and (e) maternal uterine activity, and the step of determining the present level of risk to the child for neurological injury comprises determining whether each concurrent clinical parameter (a) through (e) independently exhibits at least one non-reassuring characteristic, and transforming the number of the concurrent clinical parameters (a) through (e) that simultaneously, independently exhibit at least one non-reassuring characteristic into an indication of the present level of risk to the fetus corresponding to the number of the parameters (a) through (e) that simultaneously, independently exhibit at least one non-reassuring characteristic.

5. The method of claim 1, further comprising the steps of:
    determining at a second period in time during or before labor, later than the first period in time, a present level of risk to the fetus for neurological injury based on the first set of concurrent clinical parameters, wherein the determined present level of risk is expressed as a second FRI value; and
    determining a rate of drop from the first FRI value to the second FRI value;
    wherein further the step (d) comprises treating the fetus for which the risk of neurological injury is indicated by the step (c) and/or when the determined rate of drop is at or above a rate of drop predetermined to indicate a risk of neurological injury to the fetus.

6. The method of claim 5, wherein the first period in time during labor is characterized by a cervical dilatation of between 0-3 cm.

7. The method of claim 5, wherein the second period in time during labor is characterized by a cervical dilatation of less than or equal to 10 cm and/or up to an hour later than the first period of time.

8. The method of claim 5, wherein the risk of neurological injury to the fetus is indicated when the rate of drop is 46% or greater.

9. The method of claim 5, wherein the first set of concurrent clinical parameters comprise (a) FHR, (b) baseline FHR variability, (c) FHR accelerations, (d) FHR decelerations, and (e) maternal uterine activity, and the step of determining the present level of risk to the child for neurological injury comprises determining whether each concurrent clinical parameter (a) through (e) independently exhibits at least one non-reassuring characteristic, and transforming the number of the concurrent clinical parameters (a) through (e) that simultaneously, independently exhibit at least one non-reassuring characteristic into an indication of the present level of risk to the fetus corresponding to the number of the parameters (a) through (e) that simultaneously, independently exhibit at least one non-reassuring characteristic.

10. The method of claim 5, further comprising the step of determining a MoM for the rate of drop by dividing the rate of drop by the median rate of drop of a dataset comprising a population of rates of drop for FRI values established at the same periods in time during or before the first stage of labor as the first and second periods, and wherein further the step (d) comprises treating the fetus for which the risk of neurological injury is indicated by the step (c) and/or when the determined MoM for the rate of drop is a MoM for the rate of drop that is predetermined to indicate a risk of neurological injury to the fetus.

11. An apparatus for reducing the risk of neurological injury to a human fetus before or during labor, the apparatus comprising:
at least one computer operative to:
receive input signals indicative of at least a first set of concurrent clinical parameters indicative of a present level of risk for neurological injury to the fetus;
determine at a first period in time during or before labor a present level of risk to the fetus for neurological injury based on the first set of concurrent clinical parameters, wherein the determined present level of risk is expressed as a numerical value (the first FRI value);
determine a multiple of the median (MoM) for the first FRI value by dividing the first FRI value by the median FRI value of a dataset comprising a population of FRI values established at the same period in time during or before the first stage of labor as the first period; and
provide an output indicating a risk for neurological injury when the determined MoM of the first FRI value is a predefined multiple of the median FRI value.

12. The apparatus of claim 11, wherein the at least one computer is further operative to:
receive inputs indicating base excess (BE) values for the fetus at at least second and third periods in time during the first stage of labor, wherein the third period in time is later than the second point in time;
determine a rate of drop for the BE values at the second and third periods in time; and
provide an output indicating a risk for neurological injury when the BE values at the second and third periods in time reflect a rate of drop greater than a predefined value.

13. The apparatus of claim 12, wherein the second and third periods in time during labor are each characterized by a cervical dilatation of less than 10 cm.

14. The apparatus of claim 11, wherein:
the first set of concurrent clinical parameters comprise (a) FHR, (b) baseline FHR variability, (c) FHR accelerations, (d) FHR decelerations, and (e) maternal uterine activity; and
wherein the at least one computer is operative to determine at the first period in time whether each concurrent clinical parameter (a) through (e) independently exhibits at least one non-reassuring characteristic, and to transform the number of the concurrent clinical parameters (a) through (e) that simultaneously, independently exhibit at least one non-reassuring characteristic into the first FRI value.

15. The apparatus of claim 11, wherein the at least one computer is further operative to:
determine at a second period in time during or before labor, later than the first period in time, a present level of risk to the fetus for neurological injury based on the first set of concurrent clinical parameters, wherein the determined present level of risk is expressed as a second FRI value;
determine a rate of drop from the first FRI value to the second FRI value; and
provide an output indicating a risk for neurological injury when the determined rate of drop from the first FRI value to the second FRI value is at least a predetermined rate of drop.

16. The apparatus of claim 15, wherein the first period in time during labor is characterized by a cervical dilatation of between 0-3 cm.

17. The apparatus of claim 15, wherein the second period in time during labor is characterized by a cervical dilatation of less than or equal to 10 cm and/or up to an hour later than the first period of time.

18. The apparatus of claim 15, wherein the risk of neurological injury to the fetus is indicated when the rate of drop is 46% or greater.

19. The apparatus of claim 15, wherein:
the first set of concurrent clinical parameters comprise (a) FHR, (b) baseline FHR variability, (c) FHR accelerations, (d) FHR decelerations, and (e) maternal uterine activity; and
wherein the at least one computer is operative to determine at the first period in time whether each concurrent clinical parameter (a) through (e) independently exhibits at least one non-reassuring characteristic, and to transform the number of the concurrent clinical parameters (a) through (e) that simultaneously, independently exhibit at least one non-reassuring characteristic into the first FRI value.

20. The apparatus of claim 15, wherein the at least one computer is further operative to:
determine a MoM for the rate of drop by dividing the rate of drop by the median rate of drop of a dataset comprising a population of rates of drop for FRI values established at the same periods in time during or before the first stage of labor as the first and second periods; and
provide an output (i) indicating a risk for neurological injury when the determined MoM of the first FRI value is a predefined multiple of the median FRI value, and/or (ii) indicating the existence of neurological injury to the fetus when the MoM for the rate of drop is a predefined MoM rate of drop.

* * * * *